(12) United States Patent
Joabsson et al.

(10) Patent No.: US 9,757,461 B2
(45) Date of Patent: Sep. 12, 2017

(54) GNRH ANALOGUE FORMULATIONS

(75) Inventors: Fredrik Joabsson, Lund (SE); Markus Johnsson, Lund (SE); Fredrik Tiberg, Lund (SE)

(73) Assignee: CAMURUS AB (SE)

( * ) Notice: Subject to any disclaimer, the term of this patent is extended or adjusted under 35 U.S.C. 154(b) by 693 days.

(21) Appl. No.: 11/795,250

(22) PCT Filed: Dec. 9, 2005

(86) PCT No.: PCT/GB2005/004752
§ 371 (c)(1),
(2), (4) Date: Mar. 24, 2008

(87) PCT Pub. No.: WO2006/075125
PCT Pub. Date: Jul. 20, 2006

(65) Prior Publication Data
US 2009/0170782 A1    Jul. 2, 2009

(30) Foreign Application Priority Data

Jan. 14, 2005  (GB) .................................. 0500807.3
Apr. 18, 2005  (GB) .................................. 0507811.8
Jun. 6, 2005   (WO) ................. PCT/GB2005/002217

(51) Int. Cl.
| | | |
|---|---|---|
| C07K 7/00 | (2006.01) |
| A61K 47/24 | (2006.01) |
| A61K 8/02 | (2006.01) |
| A61K 8/34 | (2006.01) |
| A61K 8/37 | (2006.01) |
| A61K 8/49 | (2006.01) |
| A61K 8/55 | (2006.01) |
| A61K 9/00 | (2006.01) |
| A61K 9/12 | (2006.01) |
| A61K 9/127 | (2006.01) |
| A61K 9/70 | (2006.01) |
| A61K 31/155 | (2006.01) |
| A61K 31/416 | (2006.01) |
| A61K 45/06 | (2006.01) |
| A61Q 19/00 | (2006.01) |
| A61K 8/92 | (2006.01) |
| A61K 31/191 | (2006.01) |
| A61K 47/44 | (2017.01) |
| A61Q 17/04 | (2006.01) |
| A61K 8/21 | (2006.01) |
| A61K 31/196 | (2006.01) |
| A61K 31/198 | (2006.01) |
| A61K 31/4025 | (2006.01) |
| A61K 31/4468 | (2006.01) |
| A61K 31/5513 | (2006.01) |

(Continued)

(52) U.S. Cl.
CPC ............ *A61K 47/24* (2013.01); *A61K 8/0295* (2013.01); *A61K 8/21* (2013.01); *A61K 8/34* (2013.01); *A61K 8/37* (2013.01); *A61K 8/375* (2013.01); *A61K 8/494* (2013.01); *A61K 8/553* (2013.01); *A61K 8/92* (2013.01); *A61K 9/006* (2013.01); *A61K 9/0014* (2013.01); *A61K 9/0043* (2013.01); *A61K 9/0048* (2013.01); *A61K 9/0063* (2013.01); *A61K 9/12* (2013.01); *A61K 9/1274* (2013.01); *A61K 9/7015* (2013.01); *A61K 31/155* (2013.01); *A61K 31/191* (2013.01); *A61K 31/196* (2013.01); *A61K 31/198* (2013.01); *A61K 31/4025* (2013.01); *A61K 31/416* (2013.01); *A61K 31/4468* (2013.01); *A61K 31/5513* (2013.01); *A61K 38/23* (2013.01); *A61K 45/06* (2013.01); *A61K 47/10* (2013.01); *A61K 47/14* (2013.01); *A61K 47/22* (2013.01); *A61K 47/44* (2013.01); *A61Q 11/00* (2013.01); *A61Q 17/04* (2013.01); *A61Q 19/00* (2013.01); *A61K 2800/48* (2013.01); *A61K 2800/59* (2013.01)

(58) Field of Classification Search
None
See application file for complete search history.

(56) References Cited

U.S. PATENT DOCUMENTS

| | | |
|---|---|---|
| 4,938,763 A | 7/1990 | Dunn et al. |
| 5,340,802 A | 8/1994 | Shiosaki et al. |

(Continued)

FOREIGN PATENT DOCUMENTS

| | | |
|---|---|---|
| EP | 1600162 | 11/2005 |
| WO | WO 93/06921 A1 | 4/1993 |

(Continued)

OTHER PUBLICATIONS

Indications and Usage of Eligard, pp. 1-5, print out from http://www.rxlist.com.

(Continued)

*Primary Examiner* — Michael Pak
(74) *Attorney, Agent, or Firm* — J.A. Lindeman & Co., PLLC

(57) ABSTRACT

The present invention relates to compositions forming a low viscosity mixture of: a) at least one diacyl glycerol; b) at least one phosphatidyl choline; c) at least one oxygen containing organic solvent; d) at least one GnRH analog; Wherein the pre-formulation forms, or is capable of forming, at least one liquid crystalline phase structure upon contact with an aqueous fluid. The invention further relates to methods of treatment comprising administration of such compositions, pre-filled administration devices and kits containing the formulations.

24 Claims, 1 Drawing Sheet

(51) Int. Cl.
*A61K 38/23* (2006.01)
*A61K 47/10* (2017.01)
*A61K 47/14* (2017.01)
*A61K 47/22* (2006.01)
*A61Q 11/00* (2006.01)

(56) References Cited

U.S. PATENT DOCUMENTS

| | | | |
|---|---|---|---|
| 5,480,656 | A | 1/1996 | Okada et al. |
| 5,531,925 | A | 7/1996 | Landh et al. |
| 5,639,480 | A | 6/1997 | Bodmer et al. |
| 5,776,885 | A | 7/1998 | Orsolini et al. |
| 5,807,573 | A | 9/1998 | Ljusberg-Wahren et al. |
| 5,955,502 | A | 9/1999 | Hansen et al. |
| 6,066,328 | A | 5/2000 | Ribier et al. |
| 6,113,943 | A | 9/2000 | Okada et al. |
| 6,228,383 | B1 | 5/2001 | Hansen et al. |
| 6,458,924 | B2 | 10/2002 | Knudsen et al. |
| 6,464,987 | B1 | 10/2002 | Fanara et al. |
| 8,097,239 | B2 | 1/2012 | Johnsson et al. |
| 8,182,834 | B2 | 5/2012 | Johnsson et al. |
| 8,187,629 | B2 | 5/2012 | Barauskas et al. |
| 8,236,292 | B2 | 8/2012 | Thuresson et al. |
| 8,236,755 | B2 | 8/2012 | Thuresson et al. |
| 2002/0026027 | A1* | 2/2002 | Ansell ............... 528/66 |
| 2003/0022242 | A1 | 1/2003 | Anderson |
| 2004/0018241 | A1 | 1/2004 | Houze et al. |
| 2004/0201117 | A1 | 10/2004 | Anderson |
| 2005/0136059 | A1* | 6/2005 | Thorpe et al. ......... 424/155.1 |
| 2006/0073203 | A1 | 4/2006 | Ljusberg-Wahren et al. |
| 2007/0080323 | A1 | 4/2007 | Joabsson et al. |
| 2007/0110777 | A1 | 5/2007 | Joabsson et al. |
| 2007/0134336 | A1 | 6/2007 | Worle et al. |
| 2007/0231374 | A1 | 10/2007 | Tiberg et al. |
| 2008/0124394 | A1 | 5/2008 | Johnsson et al. |
| 2008/0146490 | A1 | 6/2008 | Joabsson et al. |
| 2008/0161276 | A1 | 7/2008 | Johnsson et al. |
| 2008/0214995 | A1* | 9/2008 | Boyd et al. ................ 604/68 |
| 2008/0274176 | A1 | 11/2008 | Johnsson et al. |
| 2009/0069221 | A1 | 3/2009 | Joabsson et al. |
| 2009/0155193 | A1 | 6/2009 | Joabsson et al. |
| 2010/0210519 | A1 | 8/2010 | Johnsson et al. |
| 2011/0230569 | A1 | 9/2011 | Nistor et al. |
| 2012/0028890 | A1 | 2/2012 | Nistor et al. |
| 2012/0269772 | A1 | 10/2012 | Thuresson et al. |

FOREIGN PATENT DOCUMENTS

| | | |
|---|---|---|
| WO | WO 95/34287 A1 | 12/1995 |
| WO | 97/13528 | 4/1997 |
| WO | 98/47487 | 10/1998 |
| WO | WO 02/02716 A2 | 1/2002 |
| WO | WO 02/066014 A2 | 8/2002 |
| WO | WO 02/068561 A2 | 9/2002 |
| WO | WO 02/068562 A2 | 9/2002 |
| WO | WO 03/002136 A2 | 1/2003 |
| WO | WO 03/057235 A2 | 7/2003 |
| WO | WO 2004/087215 | 10/2004 |
| WO | WO 2005/014162 A1 | 2/2005 |
| WO | WO 2005/021022 A2 | 3/2005 |
| WO | 2005/046642 | 5/2005 |
| WO | WO 2005/048952 A2 | 6/2005 |
| WO | WO 2005/063213 A1 | 7/2005 |
| WO | 2005/070394 | 8/2005 |
| WO | WO 2005/117830 | 12/2005 |
| WO | WO 2006/075123 A1 | 7/2006 |
| WO | WO 2006/075124 A1 | 7/2006 |
| WO | WO 2006/075125 A1 | 7/2006 |
| WO | WO 2006/077362 A1 | 7/2006 |
| WO | WO 2006/131730 A1 | 12/2006 |
| WO | WO 2008/152401 A1 | 12/2008 |
| WO | WO 2009/024795 A1 | 2/2009 |
| WO | WO 2009/024797 A1 | 2/2009 |
| WO | WO 2010/020794 A1 | 2/2010 |

OTHER PUBLICATIONS

PDR Information on Eligard 30 mg(Sanofi-Synthelabo), print out from www.Drugs.com , pp. 1-14.
Pharmaceutical Information on LUPRON DEPOT, print out from www.rxmed.com , pp. 1-8.
Information on Goserelin Acetate print out form http://www.bachem.com/.
J. G. M. Klijn et al., "Combined tamoxifen and luteinizing hormone-releasing hormone (LHRH) agonist versus LHRH agonist alone in premenopausal advanced breast cancer: A meta-analysis of four randomized trials", Journal of Clinical Oncology, 2001, vol. 19, No. 2, pp. 343-353 (Abstract only).
Information on Goserelin Subcutaneous, Monograph—Goserelin Acetate, pp. 1-7, print out form www.medscape.com.
Product Information on Zoladex Goserelin Acetate Implant (Equivalent to 10.8 mg goserelin).
Information on Leuprolide Intramuscular, Monograph—Leuprolide Acetate, pp. 1-20, print out for www.medscape.com.
Information on Leuprolide (3 Month) Intramuscular, Monograph—Leuprolide Acetate, pp. 1-20, print out from www.medscape.com.
Product Specification of Leuprolide by GL Biochem, print out from http://www.glschina.com.
Chang, J., "Use of GnRH agonists in the treatment of hyperandrogenism and hirsutism", print out from http://patients.uptodate.com.
R. Berges, "Eligard: Pharmacokinetics, Effect on Testosterone and PSA Levels and Tolerability", European Urology Supplements, 2005, vol. 4, pp. 20-25.
K. J. Schuh et al., "Onset, magnitude and duration of opioid blockade produced by buprenorphine and naltrexone in humans", Psychopharmacology, (Berl), Jul. 1999, vol. 145, No. 2, pp. 162-174 (Abstract only).
Information About Buprenorphine Therapy, print out from http://buprenorphine.samhsa.gov/about.html, pp. 1-4.
"Leutinizing Hormone Releasing Hormone (LHRH) Agonists: Goserelin (Zoladex) vs. Leuprolide (Lupron) for Prostate Cancer", DoD Pharmacoeconomic Center Update, Newsletter, Dec. 2000, vol. 1, No. 1, print out from http://www.pec.ha.osd.mil.com, pp. 1-3.
S. V. Welin et al., "High-dose treatment with a long-acting somatostatin analogue in patients with advanced midgut carcinoid tumours", European Journal of Endocrinology, 2004, vol. 151, pp. 107-112.
O. Sartor "Eligard: Leuprolide Acetate in a Novel Sustained-Release Delivery System", Urology, 2003, vol. 61, (Supplement 2A), pp. 25-31.
About Sandostatin: Proven Control of GH, 1GF-1 and Gastrointestinal Hormone, from www.sandostatin.com/about.sandostatin/index.html and linked documents.
"Acromegaly" from www.niddk.nil.gov/health/endo/pubs/acro/acro.htm.
American Peptide Company, Product Details "Somatostatin and analogs," from www.americanpeptide.com/.
N. Ardjomand et al., "Expression of Somatostatin Receptors in uveal melanomas," Inv. Opthalmol. & Vis. Sci., 2003, vol. 44, No. 3, pp. 980-987.
Barauskas et al., Pharmaceutical Nanotechnology, "Interactions of lipid-based liquid crystalline nanoparticles with model and cell membranes," International Journal of Pharmaceutics 391 (2010) pp. 284-291.
P. Chanson et al., "Comparison of octreotide acetate LAR and lanreptide SR in patients with acromegaly," Clin. Endocrinology, 2001, vol. 54, No. 1, pp. 11-13, (Abstract only).
Comets et al., "Non parametric analysis of the absorption profile of octreotide in rabbits from long-acting release formulation OncoLAR," J. Controlled Release 59:197-205 (1999).
F. Dall'Antonia, "Structure determination of organo-silicon compounds.", pp. 6 to 8 from http://shelx.uni-ac.gwdg.de/-fabio/endwkcon.htm.
Definition of analog from http://cancerweb.ncl.ac.uk!omd/about.html, pp. 1-5. Accessed Jul. 7, 2005.

(56) References Cited

OTHER PUBLICATIONS

B. L. Erstad, "Octreotide for acute variceal bleeding," Ann. Pharmacother., 2001, vol. 35, No. 5, pp. 618-626. (Abstract only).
FDA's 510(k) Summary of Camurus AB, episil® K101769.
A. K. Flogstad et al., "Sandostatin LAR in acromegalic patients: long term treatment," J. Clinical Endocrinology & Metabolism, 1997, vol. 82, No. 1, pp. 23-28.
P. R. Gibson & J. G. Muir, "Reinforcing the mucus: a new therapeutic approach for ulcerative colitis," Gut, 2005, vol. 54, pp. 900-903.
L. M. Grant & F. Tibert, "Normal and Lateral Forces between Lipid Covered Solids in Solution: Correlation with Layer Packing and Structure," Biophysical Journal, 2002, vol. 82, pp. 1373-1385.
B.A. Hills, "Surface-active phospholipid: a Pandora's box of clinical applications. Part II. Barrier and lubricating properties," Internal Medicine Journal, 2002, vol. 32, pp. 242-251.
G. G. Holz et al., "Glucagon-Like Peptide-1 Synthetic Analogs: New Therapeutic Agents for Use in the Treatment of Diabetes Mellitus," Current Medicinal Chemistry (2003), vol. 10, pp. 2471-2483.
H. Hui et al., "Structure and function studies of glucagon-like peptide-1 (GLP-1): the designing of a novel pharmacological agent for the treatment of diabetes," Diabetes Metabolism Research and Reviews, (2005), vol. 21, pp. 313-331.
Invitrogen, "Pluronic F-127," Molecular Probes Invitrogen Detection Technologies, pp. 1-2, 2008.
Johnsson et al., "Physicochemical and Drug Delivery Aspects of Lipid-Based Liquid Crystalline Nanoparticles: A Case Study of Intravenously Administered Propofol," Journal of Nanoscience and Nanotechnology, vol. 6, No. 9/10, pp. 3017-3024, 2006.
Kamo, et al., "Nonlamellar Liquid Crystalline Phases and Their Particle Formation in the Egg Yolk Phosphatidylcholine/Diolein System," Langmuir, vol. 19, pp. 9191-9195, Published on Web Oct. 1, 2003.
Kesisoglou, et al., "Liposomal Formulations of Inflammatory Bowel Disease Drugs: Local versus Systemic Drug Delivery in a Rat Model," Pharmaceutical Research, vol. 22, No. 8, Aug. 2005, pp. 1320-1329.
L. M. Knudsen, "Glucagon-like Peptide-1: The Basis of a New Class of Treatment for Type 2 Diabetes," J. Med. Chem. (2004), vol. 47, pp. 4128-4134.
L. M. Knudsen et al., "Potent Derivatives of Glucagon-like Peptide-1 with Pharmacokinetic Properties Suitable for Once Daily Administration," J. Med. Chem. (2000) vol. 43, pp. 1664-1669.
I. Lancranjan et al., "Sandostatin LAR: Pharmacokinetics. Pharmacodynamics, Efficacy and Tolerability in Acromegalic Patients," Metabolism, 1995, vol. 44, No. 1, pp. 18-26.
Loughrey et al., "Development of a Sensitive Sandwich ELISA for Detecting Full Length Biologically Active TH0318, a GLP-1 Analogue," presented at the 2005 AAPS Annual Meeting and Exposition, Abstract No. W5009.
Martel et al., "Enzyme Linked Immunosorbent Assay (EUSA) Method for the Determination of TH0318, a New GLP-1 Analogue in Development for Diabetes," presented at the 2005 MPS Annual Meeting and Exposition, Abstract No. W5008.
Martel et al., "Enzyme Linked !mmunosorbent Assay (EUSA) Method for the Determination of TH0318, a New GLP-1 Analogue in Development for Diabetes," Poster.
MSDS for Ethylene Glycol and Abbreviations used in Toxicity data.
Novartis Pharmaceuticals Corporation, "Sansdostatin LAR Depot (octreotide acetate for injectable suspension)", pp. 1-19.
Published Data Provided by Sandostatin LAR "The Latest Research and Treatment Information for Pituitary Disorders" from http://www.sandostatin.com/published data/index.html.
J. C. Shah et al., "Cubic phase gels as drug delivery systems," Advanced Drug Delivery Reviews, 2001, vol. 47, pp. 229-250.
"Setting new standards of care," Mixing and Administration instructions for Sandostatin LAR.
W. Stremmel et al., "Retarded release phosphatidylcholine benefits patients with chronic active ulcerative colitis," Gut, 2005, vol. 54, pp. 966-971.
A Sturm & A. U. Dignass, "Modulation of gastrointestinal wound repair and inflammation by phospholipids," Biochimica et Biophysica Acta, 2002, vol. 1582, pp. 282-288.
Svanberg et al., "A New Preventive Strategy Using a Bioadhesive Oromucosal Lipid Solution and Oral Cryotherapy to Protect the Oral Cavity—and Reduce the Need for Total Parenteral Nutrition (Tpn) for Patients Undergoing Autologous Stemcell Transplantation," Support Care Cancer 18 (Suppl 3):S114-S115, at Abstract 08-076 (2010) (attached hereto as Annex 5 to Evidentiary Declaration Under 37 C.F.R. § 1.132 of Fredrik Tiberg).
Tiberg et al., "Drug delivery applications of non-lamellar liquid crystalline phases and nanoparticles", J. Drug Del Sci. Tech., 21(1) pp. 101-109, 2011.
Tiberg et al., "Treatment of oral mucositis pain by a bioadhesive barrier forming lipid solution," Camurus (attached hereto as Annex 3 to Evidentiary Declaration Under 37 C.F.R. § 1.132 of Fredrik Tiberg).
Tiberg et al., "Treatment of Oral Mucositis Pain by a Bioadhesive Barrier Forming Lipid Solution," Support Care Center 17(7):918 (2009) (attached hereto as Annex 4 to Evidentiary Declaration Under 37 C.F.R. § 1.132 of Fredrik Tiberg).
Treating Acromegaly, from http://www.sandostatin.com/Ireating acromegaly/index.html and linked documents.
Wermuth, Pure and Appl. Chem, 1998, 70, 1129-1143.
E. Woltering et al., "Octreotide acetate (LAR) dose effect on plasma octreotide levels: Impact on neuroendocrine tumor Management," F. Clin Oncology, 2005 ASCO Annual Meeting Proceedings, vol. 23, No. 16S, pp. 3177 (Abstract only).
E. A. Woltering, "A discussion on the utility of various routes of administration of octreotide acetate," from http://www.carcinoid.org/medpro/docs/WoltPump2005.htm.
International Search Report of PCT/GB2005/004745 dated May 8, 2006.
International Preliminary Report on Patentability of PCT/GB2005/004745 dated Jul. 20, 2007.
Written Opinion of PCT/GB2005/004745 dated May 8, 2006.
International Search Report of PCT/GB2005/04748 dated Mar. 23, 2006.
International Preliminary Report on Patentability of PCT/GB2005/04748 dated Mar. 12, 2007.
Written Opinion of PCT/GB2005/04748 dated Mar. 23, 2006.
International Search Report of PCT/GB2005/04752 dated Mar. 17, 2006.
International Preliminary Report on Patentability of PCT/GB2005/04752 dated Mar. 12, 2007.
Written Opinion of PCT/GB2005/04752 dated Mar. 17, 2006.
International Search Report of PCT/GB2005/004746 dated Mar. 16, 2006.
International Preliminary Report on Patentability and Written Opinion of PCT/GB2005/004746 dated Jul. 17, 2007.
International Search Report of PCT/GB2006/002079 dated Aug. 25, 2006.
International Preliminary Report on Patentability and Written Opinion of PCT/GB2006/002079 dated Dec. 6, 2007.
International Search Report of PCT/GB2008/002035 dated Oct. 6, 2008.
International Preliminary Report on Patentability of PCT/GB2008/002035 Dec. 17, 2009.
Written Opinion of PCT/GB2008/002035 dated Oct. 6, 2008.
International Search Report of PCT/GB2008/002857 dated Jan. 28, 2009.
International Preliminary Report on Patentability and Written Opinion of PCT/GB2008/002857 dated Feb. 24, 2010.
International Search Report of PCT/GB2009/002054 dated Nov. 30, 2009.
International Preliminary Report on Patentability and Written Opinion of PCT/GB2009/002054 dated Feb. 22, 2011.
Office Action in U.S. Appl. No. 11/795,243 dated May 12, 2011.
Office Action in U.S. Appl. No. 11/795,243 dated Mar. 22, 2012.
Office Action in U.S. Appl. No. 11/795,249 dated Jul. 19, 2011.

(56) References Cited

OTHER PUBLICATIONS

Office Action in U.S. Appl. No. 11/795,249 dated Oct. 25, 2010.
Office Action in U.S. Appl. No. 11/795,242 dated Jan. 10, 2013.
Office Action in U.S. Appl. No. 11/795,242 dated Dec. 23, 2011.
Office Action in U.S. Appl. No. 11/908,740 dated Feb. 14, 2012.
Office Action in U.S. Appl. No. 11/877,935 dated Dec. 21, 2010.
Office Action in U.S. Appl. No. 21/664,835 dated Feb. 12, 2013.
Apr. 23, 2014, Office Action in U.S. Appl. No. 11/795,243.

* cited by examiner

GNRH ANALOGUE FORMULATIONS

The present invention relates to formulation precursors (pre-formulations) for the in situ generation compositions for the controlled release of active agents such as GnRH agonists and/or antagonists and methods of treatment with such formulations. In particular, the invention relates to pre-formulations of amphiphilic components and at least one GnRH agonist and/or antagonist, or other active agent for parenteral application, which undergo phase transition upon exposure to aqueous fluids, such as body fluids, thereby forming a controlled release matrix.

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable or necessary, since self-administration may be difficult and thus cause inconvenience and/or poor compliance. In such cases it would be advantageous for a single administration to provide active agent at a therapeutic level over the whole period during which activity is needed.

Gonadotropin-releasing hormone (GnRH) (also known as Luteinizing hormone-releasing hormone (LHRH) and gonadorelin) is a naturally occurring deca-peptide hormone which acts largely on the pituitary gland in humans. The effect of GnRH is release pituitary hormones such as luteinizing hormone (LH) and follicle-stimulating hormone (FSH) and to contribute to the hormonal control of processes such as ovulation. The release of LH (also known as gonadotrophin) promotes ovarian and testicular steroidogenesis and thus controls levels of progesterone, estrogen and testosterone/dihydrotestosterone (DHT).

GnRH itself is a post-translationally modified decapeptide of structure pyro-Glu-His-Trp-Ser-Tyr-Gly-Leu-Arg-Pro-Gly-NH$_2$ (GnRH-I). Two natural varients are also known, GnRH-II having 5-His, 7-Trp, 8-Tyr substitutions and GnRH-III having 7-Trp, 8-Leu. Several peptide analogues with agonistic properties are known, most of which have the 10-Gly-NH$_2$ replaced with N-Et-NH$_2$. Fertirelin has 10-Gly to N-Et-NH$_2$ substitution only, while analogues having additional substitutions over GnRH-include Leuprorelin (Leuprolide), (6-D-Leu), Buserelin (6-Ser(Bu$^t$)), Histrelin (6-d-His(Imbzl)), Deslorelin (6-d-Trp). Another common nonapeptide agonist is Goserelin which is substituted with 6-Ser (Bu$^t$) and has 10-Gly-NH$_2$ replaced by AzaGly-NH$_2$. Narafelin (6-d-Nal) and Triptorelin (6-d-Trp) both retain the 10-Gly-NH$_2$ group. The structures of the two most common GnRH agonists (Leuprolide and Goserelin) are shown below.

Leuprolide: pyro-Glu-His-Trp-Ser-Tyr-D-Leu-Leu-Arg-Pro-N-Et-NH$_2$ (acetate)

Goserelin: pyro-Glu-His-Trp-Ser-Tyr-D-Ser(Bu$^t$)-Leu-Arg-Pro-Azgly-NH$_2$ (acetate)

A small number of GnRH antagonists are also known, again based on the GnRH-I structure. These include Abarelix (D-Ala-D-Phe-D-Ala-Ser-Tyr-D-Asp-Leu-Lys($^i$Pr)-Pro-D-Ala), Antarelix (D-Nal-D-Phe-D-Pal-Ser-Phe-D-Hcit-Leu-Lys($^i$Pr)-Pro-D-Ala); Cetrorelix (D-Nal-D-Phe-D-Pal-Ser-Tyr-D-Cit-Leu-Arg-Pro-D-Ala), Ganirelix (D-Nal-D-Phe-D-Pal-Ser-Tyr-D-hArg-Leu-HArg-Pro-D-Ala), Itrelix (D-Nal-D-Phe-D-Pal-Ser-NicLys-D-NicLys-Leu-Lys($^i$Pr)-Pro-D-Ala) and Nal-Glu (D-Nal-D-Phe-D-Pal-Ser-D-Glu-D-Glu-Leu-Arg-Pro-D-Ala).

Administration of single doses of a GnRH agonist, such as leuprolide, stimulates pituitary release of gonadotropins (i.e., LH and FSH), resulting in increased serum LH and FSH concentrations and stimulation of ovarian and testicular steroidogenesis. Transient increases in serum testosterone and dihydrotestosterone (DHT) in males and in serum estrone and estradiol concentrations in premenopausal females are observed during initial therapy with single daily doses of the drug.

Although the effect of a potent GnRH agonist during short-term and/or intermittent therapy is stimulation of steroidogenesis, the principal effect of the drug in animals and humans during long-term administration is inhibition of gonadotropin secretion and suppression of ovarian and testicular steroidogenesis. The exact mechanism(s) of action has not been fully elucidated, but continuous therapy with a GnRH agonist apparently produces a decrease in the number of pituitary GnRH and/or testicular LH receptors, resulting in pituitary and/or testicular desensitization, respectively. The drug does not appear to affect receptor affinity for gonadotropins. Leuprolide's mechanism of action may also involve inhibition and/or induction of enzymes that control steroidogenesis. Other mechanisms of action may include secretion of an LH molecule with altered biologic activity or impairment of normal pulsatile patterns of LH and FSH secretion.

A number of serious medical indications are related to and/or affected by the concentration of gonadal steroid hormones. These include certain neoplastic diseases, including cancers, especially of the breast and prostate, and benign prostatic hypertrophy; premature or delayed puberty in adolescents; hirsuitism; alzheimer's disease; and certain conditions relating to the reproductive system, such as hypogonadism, anovulation, amenorrhea, oligospermia, endometriosis, leiomyomata (uterine fibroids), premenstrual syndrome, and polycystic ovarian disease. Control of this system is also important in in vitro fertilisation methods.

Although treatment with a GnRH agonist might be expected to exacerbate conditions affected by gonadal steroid hormone concentration, the down-regulation effect discussed above results in the decrease of these hormones to castrate level if therapy is continued for around 2 weeks or longer. As a result, hormone-receptive tumours such as certain prostate and breast cancer, as well as precoucious puberty and many of the other conditions mentioned above can be improved or palliated by long-term GnRH agonist therapy.

Evidently, treatments involving long-term, ongoing therapy, especially where intermittent dosing could provide a reversal of the effect desired, require careful monitoring and patient compliance in order to ensure that the desired effect is achieved. The need for stable, long-term dosing with GnRH agonists had led to the development of a small number of sustained release formulations, particularly of the analogue Leuprolide (see above). The most recently introduced Leuprolide based product is Eligard (Atrix Laboratories), which comprises a poly(DL-lactide-co-glycolide) (PLG) polymer formulation dissolved in N-methyl-pyrrolidone (NMP), to which leuprolide is added shortly before administration. Eligard is available as 1-month, 3-month and 4-month slow-release products. The principal disadvantages of this delivery system are in the nature of the delivery vehicle and the complexity of administration. A leuprolide depot product called Lupron and a triptorelin depot product called Trelstar LA are also available, which are administered as suspensions of PLGA microspheres. Again, the administration is complex and the nature of the depots is not ideal.

In particular, the Eligard system is supplied in two joinable syringes, contained in a kit including three pouches, stoppers, needles and replacement plunger-rods. The composition can be stored for only 5 days without refrigeration and must be made up and administered within 30 minutes. The mixing and administration requires some 17 separate steps, including removing and replacing syringe plunger rods, joining the two syringes and mixing by transferring the contents repeatedly between them. Evidently, this method requires a medical practitioner of considerable experience for successful administration, and even in practiced hands will take a significant time to carry out the procedure. It would be a considerable advantage, therefore, to provide a depot product of similar performance in a "ready to administer" form, preferably as a simple injectable liquid which could be administered directly by no more than routine injection technique.

Existing GnRH analogue slow-release formulations must also be administered by means of a sizable needle, typically of 20-gauge or wider. This is necessary as a result of the nature of the polymeric dosing systems used, which are typically polymer dispersions or suspensions of polymeric microspheres. Evidently, it would be an advantage to provide a system of low viscosity, homogeneous solution, which could be administered easily through a narrow needle, thus decreasing the discomfort of the patient during the procedure. Reducing preparation time of health-care professionals or patients prior to the actual administration to the patient is another important issue.

The poly-lactate, poly-glycolate and poly-lactate-co-glycolate polymers typically used for degrading slow-release formulations are also the cause of some irritation in at least some patients. In particular, these polymers typically contain a certain proportion of acetic acid impurity, which will irritate the injection site on administration. When the polymer then breaks down, lactic acid and glycolic acid are the degradation products so that further irritation is caused. As a result of the combined effects of wide-needle administration and irritant contents, the discomfort at the site of administration and the formation of connective scar tissue are greater than desirable.

A further limitation of the existing GnRH analogue depot systems is that dosing cannot easily be tailored to suit particular patients. One particular indication for which GnRH analogues have been shown as effective is in the delaying of precocious puberty, but in this indication, there is a considerable variation in subject weight and a weight-tailored dose must be used. A depot system comprising a pre-weighted dry powder, which is dissolved or dispersed in an injection vehicle by means of a pair of linked syringes, does not allow any such control, however, unless a considerable range of pre-measured doses is to be provided. The depot formulation cannot be partially administered because the dissolution of the active agent within the polymer solution may not be even. It would thus be a considerable advantage to have a homogeneous depot precursor, which allowed administration of a dose to be decided on a subject-specific basis at the time of administration.

From a drug delivery point of view, polymer depot compositions generally have the disadvantage of accepting only relatively low drug loads and having a "burst/lag" release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, then drop back through the bottom of the functional window during the lag period before reaching a sustained functional concentration. Evidently, from a functional and toxicological point of view this burst/lag release profile is undesirable and could be dangerous. It may also limit the equilibrium concentration which can be provided due to the danger of adverse effects at the "peak" point.

Evidently, in the case of GnRH agonists, the time of the "burst" period, immediately after administration is the time when the composition is having precisely the opposite effect to that desired once equilibrium has established. When first administered, the agonistic properties cause a transient increase in steroid hormone production, which, in the case of advanced prostate cancer, for example, can cause an exacerbation of the symptoms of urinary problems or even paralysis. There have been reports of patients who have died as a result of this initial phase, even without any "burst" effect and so evidently it would be preferable to avoid a burst before maintenance is established. Moreover, an unnecessary high quantity of peptide is given to patients in the initial "burst" phase possibly resulting in toxic effects and an increased cost of goods.

The manufacture of PLGA microbeads and suspensions is additionally a considerable difficulty with certain existing depot systems. In particular, since the beads are particulate, and polymers clog membranes, they cannot generally be sterile-filtered and furthermore, since the PLGA copolymer melts at around 40° C., they cannot be heat-treated for sterility. As a result, a complex manufacturing process must all be conducted under conditions of high sterility.

The present inventors have now established that by providing a pre-formulation comprising certain amphiphilic components, at least one GnRH analogue and a biologically tolerable solvent in a low viscosity phase, such as molecular solution, a pre-formulation may be generated addressing many of the shortfalls of previous GnRH analogue depot formulations. In particular, the pre-formulation is easy to manufacture, may be sterile-filtered, has low viscosity (allowing easy and less painful administration typically through a narrow needle), allows a high level of bioactive agent to be incorporated (thus potentially allowing a smaller amount of composition to be used), requires shallower injection and/or forms a desired non-lamellar depot composition in vivo having a controllable "burst" or "non-burst" release profile. The compositions are also formed from materials that are non-toxic, biotolerable and biodegradable, which can be administered by i.m., s.c. and various cavities.

In a first aspect, the present invention thus provides a pre-formulation comprising a low viscosity mixture of:
a) at least one diacyl glycerol;
b) at least one phosphatidyl choline;
c) at least one oxygen containing organic solvent;
d) at least one GnRH analogue;
wherein the pre-formulation forms, or is capable of forming, at least one liquid crystalline phase structure upon contact with an aqueous fluid.

Generally, the aqueous fluid will be a body fluid particularly extra-vascular fluid, extracellular fluid/interstitial fluid or plasma, and the pre-formulation will form a liquid crystalline phase structure when contacted with such a fluid (e.g. in vivo). The pre-formulation of the invention will generally not contain any significant quantity of water prior to administration.

In a second aspect of the invention, there is also provided a method of delivery of a GnRH analogue to a human or non-human animal (preferably mammalian) body, this method comprising parenterally administering (e.g. i.m. or preferably s.c.) a pre-formulation comprising a low viscosity mixture of:
a) at least one diacyl glycerol;
b) at least one phosphatidyl choline;
c) at least one oxygen containing organic solvent;
d) at least one GnRH analogue;
whereby to form at least one liquid crystalline phase structure upon contact with an aqueous fluid in vivo following administration. Preferably, the pre-formulation administered in such a method is a pre-formulation of the invention as described herein.

In a further aspect, the present invention also provides a method for the preparation of a liquid crystalline depot composition comprising exposing a pre-formulation comprising a low viscosity mixture of:
a) at least one diacyl glycerol;
b) at least one phosphatidyl choline;
c) at least one oxygen containing organic solvent;
d) at least one GnRH analogue;
to an aqueous fluid in vivo.

Preferably the pre-formulation administered is a pre-formulation of the present invention as described herein.

In a still further aspect the present invention provides a process for the formation of a pre-formulation suitable for the administration of a bioactive agent to a (preferably mammalian) subject, said process comprising forming a low viscosity mixture of
a) at least one diacyl glycerol;
b) at least one phosphatidyl choline;
c) at least one oxygen containing organic solvent;
and dissolving or dispersing at least one GnRH analogue in the low viscosity mixture, or in at least one of components a, b or c prior to forming the low viscosity mixture. Preferably the pre-formulation so-formed is a formulation of the invention as described herein.

In a yet still further aspect the present invention provides the use of a low viscosity mixture of:
a) at least one diacyl glycerol;
b) at least one phosphatidyl choline;
c) at least one oxygen containing organic solvent;
d) at least one GnRH analogue;
in the manufacture of a pre-formulation for use in the sustained administration of said GnRH analogue, wherein said pre-formulation is capable of forming at least one liquid crystalline phase structure upon contact with an aqueous fluid.

In a still further aspect, the present invention provides a method for the treatment of a human or non-human mammalian subject in need thereof with a GnRH analogue, said method comprising administering to said subject a pre-formulation comprising a low-viscosity mixture of;
a) at least one diacyl glycerol;
b) at least one phosphatidyl choline;
c) at least one oxygen containing organic solvent;
d) at least one GnRH analogue;

Preferably, the method of treatment is a method for the treatment of at least one condition selected from neoplastic diseases, including cancers, especially of the breast and prostate, and benign prostatic hypertrophy; premature or delayed puberty in adolescents; hirsuitism; alzheimer's disease; and certain conditions relating to the reproductive system, such as hypogonadism, anovulation, amenorrhea, oligospermia, endometriosis, leiomyomata (uterine fibroids), premenstral syndrome, and polycystic ovarian disease. The method may also be an in vitro fertilisation method (IVF).

In a yet further aspect, the present invention provides the use of;
a) at least one diacyl glycerol;
b) at least one phosphatidyl choline;
c) at least one oxygen containing organic solvent;
d) at least one GnRH analogue;
in the manufacture of a low viscosity pre-formulation medicament for use in the in vivo formation of a depot for treatment of neoplastic diseases, including cancers, especially of the breast and prostate, and benign prostatic hypertrophy; premature or delayed puberty in adolescents; hirsuitism; alzheimer's disease; and certain conditions relating to the reproductive system, such as hypogonadism, anovulation, amenorrhea, oligospermia, endometriosis, leiomyomata (uterine fibroids), premenstral syndrome, or polycystic ovarian disease, or for use as part of IVF treatment.

The pre-formulations of the present invention are highly advantageous in that they are stable to prolonged storage in their final "administration ready" form. As a result, they may readily be supplied for administration either by health professionals or by patients or their carers, who need not be fully trained health professionals and may not have the experience or skills to make up complex preparations.

In a yet further aspect, the present invention provides a disposable administration device (which is also to include a device component) pre-loaded with a measured dose of a pre-formulation of the present invention. Such a device will typically contain a single dose ready for administration and will generally be sterile-packed such that the composition is stored within the device until administration. Suitable devices include cartridges, ampoules and particularly syringes and syringe barrels, either with integral needles or with standard (e.g. luer) fittings adapted to take a suitable disposable needle.

The pre-filled devices of the invention may also suitably be included in an administration kit, which kit also forms a further aspect of the invention. In a still further aspect, the invention thus provides a kit for the administration of at least one GnRH analogue, said kit containing a measured dose of a formulation of the invention and optionally an administration device or component thereof. Preferably the dose will be held within the device or component, which will be suitable for i.m. or preferably s.c. administration. The kits may include additional administration components such as needles, swabs, etc. and will optionally and preferably contain instructions for administration. Such instructions will typically relate to administration by a route as describe herein and/or for the treatment of a disease indicated herein above.

The formulations of the present invention generate a non-lamellar liquid crystalline phase following administration. The use of non-lamellar phase structures (such as liquid crystalline phases) in the delivery of bioactive agents is now relatively well established. Such structures form when an amphiphilic compound is exposed to a solvent because the amphiphile has both polar and apolar groups which cluster to form polar and apolar regions. These regions can effectively solubilise both polar and apolar compounds. In addition, many of the structures formed by amphiphiles in polar and/or apolar solvents have a very considerable area of polar/apolar boundary at which other amphiphilic compounds can be adsorbed and stabilised. Amphiphiles can also be formulated to protect active agents, to at least some extent, from aggressive biological environments, including enzymes, and thereby provide advantageous control over active agent stability and release.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the L3 phase which comprises a multiply interconnected bi-continuous network of bilayer sheets which are non-lamellar but lack the long-range order of the liquid crystalline phases. Depending upon their curvature of the amphiphile sheets, these phases may be described as normal (mean curvature towards the apolar region) or reversed (mean curvature towards the polar region).

The non-lamellar liquid crystalline and L3 phases are thermodynamically stable systems. That is to say, they are not simply a meta-stable state that will separate and/or reform into layers, lamellar phases or the like, but are the stable thermodynamic form of the lipid/solvent mixture.

It is important that the pre-formulations of the invention are not liquid crystalline prior to administration because bulk liquid crystalline phase is generally highly viscous. The pre-formulations are thus low viscosity, non-liquid-crystalline formulations which undergo a phase change upon administration to form a liquid crystalline mass. Particularly preferred examples of low viscosity mixtures are molecular solutions and/or isotropic phases such as L2 and/or L3 phases. As describe above, the L3 is a non-lamellar phase of interconnected sheets which has some phase structure but lacks the long-range order of a liquid crystalline phase. Unlike liquid crystalline phases, which are generally highly viscous, L3 phases are of lower viscosity. Obviously, mixtures of L3 phase and molecular solution and/or particles of L3 phase suspended in a bulk molecular solution of one or more components are also suitable. The L2 phase is the so-called "reversed micellar" phase or microemulsion. Most preferred low viscosity mixtures are molecular solutions, L3 phases and mixtures thereof. L2 phases are less preferred, except in the case of swollen $L_2$ phases as described below.

As used herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a small gauge needle. Preferably, the low viscosity mixtures can be dispensed through a needle of 19 awg, preferably smaller than 19 gauge, more preferably 23 awg (or most preferably even 27 gauge) needle by manual pressure. In a particularly preferred embodiment, the low viscosity mixture should be a mixture capable of passing through a standard sterile filtration membrane such as a 0.22 μm syringe filter. A typical range of suitable viscosities would be, for example, 0.1 to 5000 mPas, preferably 1 to 1000 mPas at 20° C.

It has been observed that by the addition of small amounts of low viscosity solvent, as indicated herein, a very significant change in viscosity can be provided. As indicated in FIG. 1, for example, the addition of only 5% solvent to a lipid mixture can reduce viscosity 100-fold and addition of 10% may reduce the viscosity up to 10,000 fold. In order to achieve this non-linear, synergistic effect, in lowering viscosity it is important that a solvent of appropriately low viscosity and suitable polarity be employed. Such solvents include those described herein infra.

The present invention provides a pre-formulation comprising components a, b, c and at least one GnRH analogue as indicated herein. The amounts of these components will typically be in the range 40-70% a), 30-60% b) and 0.1-10% c), with the GnRH analogue present at 0.1% to 10%. All % being by weight herein throughout, unless otherwise indicated. The formulations may consist of essentially only these components and in one aspect consist entirely of such components. Preferable ranges for component a) are 43-60%, particularly 45-55 and preferable ranges of component b) are 35-55%, particularly 40 to 50%.

Ratios of a:b are typically 40:60 to 70:30, preferably 45:55 to 60:40 and more preferably 48:52 to 55:45. Ratios of around 50:50 are highly effective.

The amount of solvent component c) in the preformulation will have a considerable effect upon several features. In particular, the viscosity and the rate (and duration) of release will alter significantly with the solvent level. The amount of solvent will thus be at least sufficient to provide a low viscosity mixture but will additionally be determined so as to provide the desired release rate. This may be determined by routine methods in view of the Examples below. Typically a level of 0.1 to 10% solvent will provide suitable release and viscosity properties. This will preferably be 2 to 8% and an amount of around 5% is highly effective.

It is the remarkable finding of the present inventors that the proportion of solvent in the formulation can be used to "tune" the release profile of the active agent during the first few days of release. In particular, although all formulations of the invention have a surprisingly low "burst/lag" effect (in fact there are may be no lag period at all), and reach a plateau release level within a few days (e.g. 5 days, preferably 3 days, more preferably 1 day) of injection, if a controlled "burst"/initial release of active agent is required in the first 1-2 days then this can be provided by increasing the solvent proportion to the upper region of the range given above. In contrast, in the mid- to lower-region of the range, a formulation giving a depot with essentially no burst and a rapid decline to the plateau release level is provided.

Thus, in one embodiment, the present invention provides formulations and depots containing around 0.1 to 6 wt % component c) and having a low release of the active compound during the first days after administration ("non-burst profile"). In an alternative embodiment, the present invention provides formulations and depots containing around 6.5 to 10 wt % component c) and having high initial release of the active compound during the first days after administration ("burst profile"). The low initial release ("non-burst profile") of active agent is defined such that the area under a plasma concentration against time the curve during the first 24 hours is less than 15% of the area under the curve for the entire curve (measured or extrapolated from time 0 to infinity or from time 0 to the last sampling time point), more preferably less than 10% and most preferable less than 7%. In addition, the decline to plateau plasma concentration levels after the initial peak should be rapid, such that plateau is reached with in 48 hours, more preferably within 24 hours, and most preferably within 12 hours. Conversely, a high initial release ("burst profile") is such that more than 15% of active agent is released within 24 hours and more preferably more than 20% is released during the first 24 hours. The decline to plateau will not occur until after 36 hours, more preferably after 48 hours and most preferably after 72 hours. It is preferable that each of these profiles is combined with a rapid settling of the plasma active agent concentration to "plateau" level. For example, the plasma concentration after 10 days should be no more than 50% greater or less than the average concentration over days 5 to 20. Preferably this will be no more than 30% and more preferably no more than 20%.

As indicated above, the amount of component c in the pre-formulations of the invention will be at least sufficient to provide a low viscosity mixture (e.g. a molecular solution, see above) of components a, b and c and will be easily determined for any particular combination of components by standard methods. The phase behaviour itself may be analysed by techniques such as visual observation in combination with polarized light microscopy, nuclear magnetic resonance, and cryo-transmission electron microscopy (cryo-TEM) to look for solutions, L2 or L3 phases, or liquid crystalline phases or as in the case of cryoTEM, dispersed fragments of such phases. Viscosity may be measured directly by standard means. As described above, an appropriate practical viscosity is that which can effectively be syringed and particularly sterile filtered. This will be assessed easily as indicated herein.

Component "a" as indicated herein is at least one diacyl glycerol (DAG) and thus has two non-polar "tail" groups. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include caproyl (C6:0), capryloyl (C8:0), capryl (C10:0), lauroyl (C12:0), myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

Mixtures of any number of diacyl lipids may be used as component a. Preferably this component will include at least a portion of glycerol dioleate (GDO). A highly preferred example is DAG comprising at least 50%, preferably at least 80% and even comprising substantially 100% GDO.

Since GDO and other diacyl glycerols are products derived from natural sources, there is generally a certain proportion of "contaminant" lipid having other chain lengths etc. In one aspect, GDO as used herein is thus used to indicate any commercial grade of GDO with concomitant impurities (i.e. GDO of commercial purity). These impurities may be separated and removed by purification but providing the grade is consistent this is rarely necessary. If necessary, however, "GDO" may be essentially chemically pure GDO, such as at least 80% pure, preferably at least 85% pure and more preferably at least 90% pure GDO.

Component "b" in the present invention is at least one phosphatidyl choline (PC). As with component a, this component comprises a polar head group and at least one non-polar tail group. The difference between components a and b lies principally in the polar group. The non-polar portions may thus suitably be derived from the fatty acids or corresponding alcohols considered above for component a. As with component a), the PC will contain two non-polar groups.

The phosphatidyl choline portion, even more suitably than any diacyl glycerol portion, may be derived from a natural source. Suitable sources of phospholipids include egg, heart (e.g. bovine), brain, liver (e.g. bovine) and plant sources including soybean. Such sources may provide one or more constituents of component b, which may comprise any mixture of phospholipids. Any single PC or mixture of PCs from these or other sources may be used, but mixtures comprising soy PC or egg PC are highly suitable. The PC component preferably contains at least 50% soy PC or egg PC, more preferably at least 75% soy PC or egg PC and most preferably essentially pure soy PC or egg PC.

Since the pre-formulations of the invention are to be administered to a subject for the controlled release of a GnRH analogue active agent, it is important that the components are biocompatible. In this regard, the pre-formulations of the present invention are highly advantageous since both PC and DAGs are well tolerated and are broken down in vivo into components that are naturally present in the mammalian body.

A particularly favoured combination of components a and b are GDO with PC, especially GDO with soy PC.

Component "c" of the pre-formulations of the invention is an oxygen containing organic solvent. Since the pre-formulation is to generate a depot composition following administration (e.g. in vivo), upon contact with an aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

In a preferred version, the solvent is such that a relatively small addition to the composition comprising a and b, i.e. preferably below 10%, give a large viscosity reductions of one order of magnitude or more. As described herein, the addition of 10% solvent can give a reduction of two, three or even four orders of magnitude in viscosity over the solvent-free composition, even if that composition is a solution or $L_2$ phase containing no solvent, or an unsuitable solvent such as water, or glycerol.

Typical solvents suitable for use as component c include at least one solvent selected from alcohols, ketones, esters (including lactones), ethers, amides and sulphoxides. Alcohols are particularly suitable and form the preferred class of solvents. Examples of suitable alcohols include ethanol, isopropanol and glycerol formal. Ethanol is most preferred. Monools are preferred to diols and polyols. Where diols or polyols are used, this is preferably in combination with an at least equal amount of monool or other preferred solvent. Examples of ketones include acetone, n-methyl pyrrolidone (NMP), 2-pyrrolidone, and propylene carbonate. Suitable ethers include diethylether, glycofurol, diethylene glycol monoethyl ether, dimethylisobarbide, and polyethylene glycols. Suitable esters include ethyl acetate and isopropyl acetate and dimethyl sulphide is as suitable sulphide solvent. Suitable amides and sulphoxides include dimethylacetanide (DMA) and dimethylsulphoxide (DMSO), respectively.

A highly preferred combination is soy PC, GDO and ethanol.

It is preferable that little or none of component c contains halogen substituted hydrocarbons since these tend to have lower biocompatibility. Where a portion of halogenated solvent such as dichloromethane or chloroform is necessary, this proportion will generally be minimised.

Component c as used herein may be a single solvent or a mixture of suitable solvents but will generally be of low viscosity. This is important because one of the key aspects of the present invention is that it provides pre-formulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component c (single solvent or mixture) should typically be no more than 18 mPas at 20° C. This is preferably no more than 15 mPas, more preferably no more than 10 mPas and most preferably no more than 7 mPas at 20° C.

A further advantage of the present pre-formulations is that a higher level of bioactive agent may be incorporated into the system. In particular, by appropriate choice of components a-c (especially c), high levels of active agent may be dissolved or suspended in the pre-formulations. This allows a reduction in the administered volume and thus less discomfort to subjects.

The pre-formulations of the present invention typically do not contain significant amounts of water. Since it is essentially impossible to remove every trace of water from a lipid composition, this is to be taken as indicating that only such minimal trace of water exists as cannot readily be removed. Such an amount will generally be less than 1% by weight, preferably less that 0.5% by the weight of the pre-formulation. In one preferred aspect, the pre-formulations of the invention do not contain glycerol, ethylene glycol or propylene glycol and contain no more than a trace of water, as just described.

The pre-formulations of the present invention contain one or more GnRH analogues or other active (see below)(which are intended by any reference to "active agents" herein). Since GnRH is a peptide hormone, typical GnRH analogues will be peptides, especially of 12 or fewer amino acids. Preferably such peptides will be structurally related to GnRH I, II and/or III, and/or one or more of the known analogues, including those listed here. Peptides may contain only amino acids selected from those 20 α-amino acids indicated in the genetic code, or more preferably may contain their isomers and other natural and non-natural amino acids, (generally α, β or γ amino acids) and their analogues and derivatives. Preferred amino acids include those listed above as constituents of the known GnRH analogues.

Amino acid derivatives are especially useful at the termini of the peptides, where the terminal amino or carboxylate group may be substituted by or with any other functional group such as hydroxy, alkoxy, carboxy, ester, amide, thio, amido, amino, alkyl amino, di- or tri-alkyl amino, alkyl (by which is meant, herein throughout $C_1$-$C_{12}$ alkyl, preferably $C_1$-$C_6$ alkyl e.g. methyl, ethyl, n-propyl, isopropyl, n-butyl, iso-sec- or t-butyl etc.), aryl (e.g phenyl, benzyl, napthyl etc) or other functional groups, preferably with at least one heteroatom and preferably having no more than 10 atoms in total, more preferably no more than 6.

Particularly preferred GnRH analogues are constrained peptides of 6 to 12 alpha-amino acids, of which particular examples include those indicated above, and particularly leuprolide and goserelin, of the sequences indicated above.

By "GnRH analogues", as used herein is indicated any GnRH agonist or antagonist, preferably peptides, peptide derivatives or peptide analogues. Peptide derived GnRH agonists are most preferred, such as those indicated above and especially leuprolide or goserelin.

The GnRH analogue will generally be formulated as 0.02 to 12% by weight of the total formulation. Typical values will be 0.1 to 10%, preferably 0.2 to 8% and more preferably 0.5 to 6%. A GnRH analogue content of around 1-5% is most preferable.

Doses of the GnRH analogue suitable for inclusion in the formulation, and thus the volume of formulation used will depend upon the release rate (as controlled, for example by the solvent type and amount use) and release duration, as well as the desired therapeutic level, the activity of the specific agent, and the rate of clearance of the particular active chosen. Typically an amount of 0.1 to 500 mg per dose would be suitable for providing a therapeutic level for between 7 and 180 days. This will preferably be 1 to 200 mg. For leuprolide or goserelin, the level will typically be around 1 to 120 mg (e.g. for a 30 to 180 day duration). Preferably, the amount of leuprolide will be around 0.02 to 1 mg per day between injections, for depots designed for release over 30 days to 1 year, preferably 3 to 6 months. Evidently, the stability of the active and linearity of the release rate will mean that the loading to duration may not be a linear relationship. A depot administered every 30 days might have, for example 2 to 30 mg or a 90 day depot have 6 to 90 mg of active, such as one of the GnRH analogues indicated herein.

The pre-formulations of the present invention are formulated to be administered parenterally. This administration will generally not be an intra-vascular method but will preferably be subcutaneous, intracavitary or intramuscular. Typically the administration will be by injection, which term is used herein to indicate any method in which the formulation is passed through the skin, such as by needle, catheter or needle-less injector.

Preferred parenteral administration is by i.m or s.c. injection, most preferably by deep s.c. injection. An important feature of the composition of the invention is that it can be administered both by i.m. and s.c. and other routes without toxicity or significant local effects. It is also suitable for intracavital administration. The deep s.c. injection has the advantage of being less deep and less painful to the subject than the (deep) i.m. injection used for some current depots and is technically most suitable in the present case as it combines ease of injection with low risk of local side effects. It is a surprising observation of the present inventors that the formulations provide sustained release of active agent over a predictable time period by both subcutaneous and intramuscular injection. This therefore allows the site of injection to be varied widely and allows the dose to be administered without detailed consideration of the tissue depth at the site of injection.

The pre-formulations of the present invention provide non-lamellar liquid crystalline depot compositions upon exposure to aqueous fluids, especially in vivo. As used herein, the term "non-lamellar" is used to indicate a normal or reversed liquid crystalline phase (such as a cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise.

For many combinations of lipids, only certain non-lamellar phases exist, or exist in any stable state. It is a surprising feature of the present invention that compositions as described herein frequently exhibit non-lamellar phases which are not present with many other combinations of components. In one particularly advantageous embodiment, therefore, the present invention relates to compositions having a combination of components for which an $I_2$ and/or $L_2$ phase region exists when diluted with aqueous solvent. The presence or absence of such regions can be tested easily for any particular combination by simple dilution of the composition with aqueous solvent and study of the resulting phase structures by the methods described herein.

In a highly advantageous embodiment, the compositions of the invention may form an $I_2$ phase, or a mixed phase including $I_2$ phase upon contact with water. The $I_2$ phase is a reversed cubic liquid crystalline phase having discontinuous aqueous regions. This phase is of particular advantage in the controlled release of active agents and especially in combination with polar active agents, such as water soluble actives because the discontinuous polar domains prevent rapid diffusion of the actives. Depot precursors in the $L_2$ are highly effective in combination with an $I_2$ phase depot formation. This is because the $L_2$ phase is a so-called "reversed micellar" phase having a continuous hydrophobic region surrounding discrete polar cores. $L_2$ thus has similar advantages with hydrophilic actives. In transient stages after contact with body fluid the composition can comprise multiple phases since the formation of an initial surface phase will retard the passage of solvent into the core of the depot, especially with substantial sized administrations of internal depots. Without being bound by theory, it is believed that this transient formation of a surface phase, especially a liquid crystalline surface phase, serves to dramatically reduce the "burst/lag" profile of the present compositions by immediately restricting the rate of exchange between the composition and the surroundings. Transient phases may include (generally in order from the outside towards the centre of the depot): $H_{II}$ or $L_\alpha$, $I_2$, $L_2$, and liquid (solution). It is highly preferred that the composition of the invention is capable forming at least two and more preferably at least three of these phases simultaneously at transient stages after contact with water at physiological temperatures. In particular, it is highly preferred that one of the phases formed, at least transiently, is the $I_2$ phase.

It is important to appreciate that the pre-formulations of the present invention are of low viscosity. As a result, these pre-formulations must not be in any bulk liquid crystalline phase since all liquid crystalline phases have a viscosity significantly higher than could be administered by syringe or spray dispenser. The pre-formulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 10 wt % of solvent (component c) having a viscosity reducing effect. This is in contrast to a "concentrated" or "unswollen" $L_2$ phase containing no solvent, or a lesser amount of solvent, or containing a solvent (or mixture) which does not provide the decrease in viscosity associated with the oxygen-containing, low viscosity solvents specified herein.

Upon administration, the pre-formulations of the present invention undergo a phase structure transition from a low viscosity mixture to a high viscosity (generally tissue adherent) depot composition. Generally this will be a transition from a molecular mixture, swollen $L_2$ and/or L3 phase to one or more (high viscosity) liquid crystalline phases such as normal or reversed hexagonal or cubic liquid crystalline phases or mixtures thereof. As indicated above, further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. up to 30 minutes, preferably up to 10 minutes, more preferably 5 minutes of less). The remainder of the composition may change phase to a liquid crystalline phase more slowly by diffusion and/or as the surface region disperses.

In one preferred embodiment, the present invention thus provides a pre-formulation as described herein of which at least a portion forms a hexagonal liquid crystalline phase upon contact with an aqueous fluid. The thus-formed hexagonal phase may gradually disperse and/or degrade, releasing the active agent, or may subsequently convert to a cubic liquid crystalline phase, which in turn then gradually disperses. It is believed that the hexagonal phase will provide a more rapid release of active agent, in particular of hydrophilic active agent, than the cubic phase structure, especially the $I_2$ and $L_2$ phase. Thus, where the hexagonal phase forms prior to the cubic phase, this will result in an initial release of active agent to bring the concentration up to an effective level rapidly, followed by the gradual release of a "maintenance dose" as the cubic phase degrades. In this way, the release profile may be controlled.

Without being bound by theory, it is believed that upon exposure (e.g. to body fluids), the pre-formulations of the invention lose some or all of the organic solvent included therein (e.g. by diffusion) and take in aqueous fluid from the bodily environment (e.g. the in vivo environment) such that at least a part of the formulation generates a non-lamellar, particularly liquid crystalline phase structure. In most cases these non-lamellar structures are highly viscous and are not easily dissolved or dispersed into the in vivo environment. The result is a monolithic "depot" generated in vivo with only a limited area of exposure to body fluids. Furthermore, because the non-lamellar structure has large polar, apolar and boundary regions, it is highly effective in solubilising and stabilising active agents such as peptides and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively low biological half-life (see above).

The depot systems formed by the formulations of the present invention are highly effective in protecting the active agent from degradation and thus allow an extended release period. Comparative tests have been carried out between the known PLGA slow-release product and formulations of the present invention containing GDO, soy PC, ethanol and active agents. These indicate that formulations of the present invention give lesser degradation under simulated in vivo conditions than known compositions. The formulations of the invention thus may provide in vivo depots of GnRH analogues which require administration only once every 20 to 360 days, preferably 30 to 240 days, more preferably 60 to 180 days. Evidently, a longer stable release period is desirable for patient comfort and compliance, as well as demanding less time from health professionals.

A considerable advantage of the depot precursors of the present invention is that they are stable homogeneous phases. That is to say, they may be stored for considerable periods (preferably at least 6 months) at room or refrigerator temperature, without phase separation. As well as providing advantageous storage and facile administration, this allows for the dose of GnRH analogue to be selected by reference to the species, age, sex, weight, and/or physical condition of the individual subject, by means of injecting a selected volume. Furthermore, the present inventors have surprisingly found that the initial release of active agent (observed as $C_{max}$) is not proportional to dose volume, in ranges of at least 10-fold in sample volume injection, while the total drug exposure (observed as AUC or mean plateau plasma concentration) is proportional to the injection volume. On the contrary, it has been shown that $C_{max}$ can be correlated to the surface area of the injected dose volume. That is, $C_{max}$ is proportional to the two-third power of the injected dose volume. Increasing the dose volume by a factor of 10 will not increase the $C_{max}$ 10 times and the relationship between $C_{max}$ and the total drug exposure (AUC or mean plateau plasma concentration level) will thus decrease with increasing dose volume. This is highly advantageous, because this property reduce the risk of reaching potentially toxic plasma drug concentrations even if the total dose is significantly, increased. Even in situations where dosing is not directly proportional to injection volume, however, the homogenous nature of the depot precursors importantly allow for partial administration of a pre-measured dose and this administration may be made by reference to a dosing table, chart, software calculation etc. which may take into account any or all relevant subject variables.

The present invention thus provides for methods comprising the selection of a dosing amount specific to an individual, particularly by subject weight. The means for this dose selection being by administration volume.

Furthermore, the PLGA solution-type depots formulated for long-term (e.g. 4-month) release of leuprolide show a "burst" release of the active, with a maximum concentration during the initial burst being 100-600 times that of the plateau level. As indicated above, this can have considerably disadvantages, especially with GnRH agonists, since their initial effect is to increase gonadal steroid production, which can cause symptoms to worsen.

It is an unexpected finding of the present inventors that the pre-formulations result in a depot composition that have very little "burst" effect in the active agent release profile. This is unexpected because it might be expected that the low viscosity mixture (especially if this is a solution) of the pre-composition would rapidly lose active agent upon exposure to water in the way that is observed for PLGA suspended in NMP. In fact, pre-formulations of the invention have shown considerably less of an initial "burst" than previously known polymer-base depot compositions which tend to have an initial "wash off" or "wash out" of surface-bound or dissolved active agent. In one embodiment, the invention thus provides injectable pre-formulations and resulting depot compositions wherein the highest plasma concentration of active after administration is no more than 40 times the average concentration between 24 hours and 5 days of administration. This ratio is preferably no more than 25 times and most preferably no more than 20 times (e.g. up to 10 or up to 5 times) the average concentration. This is an improvement of an order of magnitude over the existing PLGA/NMP depot product.

The compositions of the invention also allow for the generation of depot compositions with very little "lag" effect after administration. In a further embodiment, the invention thus provides injectable pre-formulations and resulting depot compositions wherein the plasma concentration of active at 7 days after a single administration is no lower than the plasma concentration of active at 21 days after administration. Similarly, the concentration of active should be higher at all times in the first 21 days than the concentration at any time from 30 days after administration onwards. This gradually decaying release profile has not previously been demonstrated for slow release GnRH analogue formulation.

In combination with the features and preferred features indicated herein, the pre-formulations of the invention may have one or more of the following preferred features independently or in combination:

Component a) comprises, consists essentially of or preferably consists of GDO;

Component b) comprises, consists essentially of or preferably consists of soy PC;

Component c) comprises, consists essentially of or preferably consists of a 1, 2, 3 or 4 carbon alcohol, preferably isopropanol or more preferably ethanol;

The pre-formulation contains at least one GnRH analogue selected from those indicated herein, preferably leuprolide, or goserelin;

The pre-formulation has a low viscosity as indicated herein.

The pre-formulation forms a liquid crystalline phase as indicated herein upon in vivo administration.

The pre-formulation generates a depot following in vivo administration, which depot releases at least one GnRH analogue at a therapeutic level over a period of at least 30 days, preferably at least 90 days, more preferably at least 180 days.

In combination with the features and preferred features indicated herein, the method(s) of treatment of the present invention may have one or more of the following preferred features independently or in combination:

The method comprises the administration of at least one formulation with one or more preferred features as indicated above;

The method comprises the administration of at least one formulation as indicated herein by i.m., s.c. or preferably deep s.c. injection;

The method comprises administration by means of a pre-filled administration device as indicated herein;

The method comprises administration through a needle no larger than 20 gauge, preferably smaller than 20 gauge, and most preferably 23 gauge or smaller;

The method comprises a single administration every 20 to 360 days, preferably 30 to 240 days, more preferably 60 to 180 days.

In combination with the features and preferred features indicated herein, the use(s) of the pre-formulations indicated herein in the manufacture of medicaments may have one or more of the following preferred features independently or in combination:

The use comprises the use of at least one formulation with one or more preferred features as indicated above;

The use comprises the manufacture of a medicament for administration of at least one formulation as indicated herein by i.m., s.c. or preferably deep s.c. injection;

The use comprises the manufacture of a medicament for administration by means of a pre-filled administration device as indicated herein;

The use comprises the manufacture of a medicament for administration through a needle no larger than 20 gauge, preferably smaller than 20 gauge, and most preferably 23 gauge or smaller;

The use comprises the manufacture of a medicament for administration once every 20 to 360 days, preferably 30 to 240 days, more preferably 60 to 180 days.

In combination with the features and preferred features indicated herein, the pre filled devices of the invention may have one or more of the following preferred features independently or in combination:

They contain a preferred formulation as indicated herein;

They comprise a needle smaller than 20 gauge, preferably no larger than 23 gauge;

They contain a single dose of 0.1 to 500 mg of GnRH analogue, preferably 1 to 200 mg;

They contain goserelin or leuprolide, at around 5 to 90 mg;

They contain a homogeneous mixture of a composition of the invention in ready-to-inject form.

They contain a total volume for administration of no more than 5 ml, preferably no more than 3 ml more preferably no more than 2 ml.

In combination with the features and preferred features indicated herein, the kits of the invention may have one or more of the following preferred features independently or in combination:

They contain a preferred formulation as indicated herein;

They contain a pre-filled device as indicated herein;

They contain a needle smaller than 20 gauge, preferably no larger than 23 gauge;

They contain a single dose of 0.1 to 500 mg of GNRH analogue, preferably 1 to 200 mg;

They contain leuprolide or goserelin, at around 5 to 90 mg;

They contain a total volume for administration of no more than 5 ml, preferably no more than 3 ml more preferably no more than 2 ml.

They contain instructions for administration by a route and/or at a frequency as indicated herein;

They contain instructions for administration for use in a method of treatment as described herein.

In Further aspects of the present invention, corresponding depot pre-formulations may be made using alternative active agents. For each of these, the types and proportions of components a), b) and c) will be as indicated above as general and preferred formulations, particularly as indicated in the attached claims, in which the appropriate doses of active agents indicated below may be substitued in place of the GnRH analogues. The formulations may be generated, tested and used by methods analogous to those for the GnRH analogues considered above, as is demonstrated in the attached examples. All aspects of the invention relating to compositions, kits and devices apply equally to the following active agents and methods of treatment apply as indicated below.

In one aspect, the invention thus provides a pre-formulation, comprising a low viscosity mixture of:
 a) at least one diacyl glycerol;
 b) at least one phosphatidyl choline;
 c) at least one oxygen containing organic solvent;
 d) risperidone or at least one analogue or derivative thereof;
wherein the pre-formulation forms, or is capable of forming, at least one liquid crystalline phase structure upon contact with an aqueous fluid.

The risperidone analogue composition will preferably be a preferred composition as indicated herein. The content of risperidone or at least one analogue or derivative thereof will typically be around 1 to 200 mg per week of depot duration, preferably 10 to 100 mg per week duration for a duration of 1 to 12 weeks.

The invention further provides a method of medical treatment comprising administration of a risperidone analogue composition as described above, preferably a method for the treatment of schizophrenia. The invention also provides the use of a risperidone analogue composition as described above in the manufacture of a medicament for the treatment of schizophrenia. The invention additionally provides for a pre-filled administration device as indicated herein and a kit as indicated herein comprising the risperidone analogue composition.

An additional and surprising aspect of the compositions of the present invention is that they can from depots for the release of non-polar small (i.e. non-peptide) molecules over a sustained period of at least 7 days, preferably at least 2 weeks and more preferably at least 4 weeks. Previously known depot compositions have generally been limited to peptides and other polar active agents and agents of high molecular weight. This applies particularly to lipid based depot compositions which have not shown sustained release of non-polar and/or small molecule actives for more than a few days previously. In this aspect of the invention, by "small molecule" is meant an active agent of molecular weight below 1,000 amu, preferably less than 800 and most preferably less than 500 amu. by non-polar is indicated a molecule with a "log P" partition coefficient between octanol and water of greater than 1, preferably greater than 2 and more preferably greater than 3. Steroid hormones such as testosterone are particularly favoured non-polar small molecules. The compositional region of around 60:40 to 40:60 a:b has been found to be the most appropriate for sustained release, for all of the actives mentioned herein, but particularly for these types of active agents. This is preferably the region 55:45 to 45:55, most preferably 52:48 to 48:52 a:b (by weight).

In a further aspect, the invention thus provides a pre-formulation, comprising a low viscosity mixture of:
 a) at least one diacyl glycerol;
 b) at least one phosphatidyl choline;
 c) at least one oxygen containing organic solvent;
 d) testosterone or at least one analogue or derivative thereof;
wherein the pre-formulation forms, or is capable of forming, at least one liquid crystalline phase structure upon contact with an aqueous fluid.

The testosterone analogue composition will preferably be a preferred composition as indicated herein. The content of testosterone or at least one analogue or derivative thereof will typically be around 5 to 100 mg per week of depot duration, preferably 10 to 70 mg per week duration for a duration of 1 to 24, preferably 8 to 16 (e.g. 12) weeks.

The invention further provides a method of treatment comprising administration of a testosterone analogue composition as described above, especially in a subject in need thereof. The method of treatment is particularly for the treatment of male hypogonadism. The invention also provides the use of a testosterone analogue composition as described above in the manufacture of a medicament for the treatment of male hypogonadism. The invention additionally provides for a pre-filled administration device as indicated herein and a kit as indicated herein comprising the testosterone analogue composition.

In another aspect, the invention thus provides a pre-formulation, comprising a low viscosity mixture of:
 a) at least one diacyl glycerol;
 b) at least one phosphatidyl choline;
 c) at least one oxygen containing organic solvent;
 d) at least one aromatase inhibitor;
 wherein the pre-formulation forms, or is capable of forming, at least one liquid crystalline phase structure upon contact with an aqueous fluid.

The aromatase inhibitor will typically be anastrazole, femara, or aromasin. The aromatase inhibitor composition will preferably be a preferred composition as indicated herein. The content of at least one aromatase inhibitor will typically be equivalent to a 3 to 10 mg oral dose per week of depot duration, which will typically be 0.03 to 1 mg pre week, preferably 0.05 to 0.8 mg per week duration, for a duration of 1 to 24, preferably 4 to 12 (e.g. 8) weeks.

The invention further provides a method of treatment comprising administration of an aromatase inhibitor composition as described above, especially in a subject in need thereof. The method of treatment is particularly for the treatment of early, locally advanced or metastatic breast cancer. The invention also provides the use of an aromatase inhibitor composition as described above in the manufacture of a medicament for the treatment of early, locally advanced or metastatic breast cancer. The invention additionally provides for a pre-filled administration device as indicated herein and a kit as indicated herein comprising the aromatase inhibitor composition.

In a further aspect, the invention also provides a pre-formulation, comprising a low viscosity mixture of:
 a) at least one diacyl glycerol;
 b) at least one phosphatidyl choline;
 c) at least one oxygen containing organic solvent;
 d) buprenorphine or at least one analogue or derivative thereof;
 wherein the pre-formulation forms, or is capable of forming, at least one liquid crystalline phase structure upon contact with an aqueous fluid.

The buprenorphine analogue composition will preferably be a preferred composition as indicated herein. The content of buprenorphine or at least one analogue or derivative thereof will typically be around 10 to 250 mg per week of depot duration, preferably 15 to 200 mg per week duration for a duration of 1 to 24, preferably 4 to 12 (e.g. 8) weeks.

The invention further provides a method of treatment comprising administration of a buprenorphine analogue composition as described above, especially in a subject in need thereof. The method of treatment is particularly for the treatment of pain, especially chronic pain, or in the treatment of opioid addiction. The invention also provides the use of a buprenorphine analogue composition as described above in the manufacture of a medicament for the treatment of for the treatment of pain, especially chronic pain, or in the treatment of opioid addiction. The invention additionally provides for a pre-filled administration device as indicated herein and a kit as indicated herein comprising the buprenorphine analogue composition.

In a still further aspect, the invention also provides a pre-formulation, comprising a low viscosity mixture of:
 a) at least one diacyl glycerol;
 b) at least one phosphatidyl choline;
 c) at least one oxygen containing organic solvent;
 d) fentanyl or at least one analogue or derivative thereof;
 wherein the pre-formulation forms, or is capable of forming, at least one liquid crystalline phase structure upon contact with an aqueous fluid.

The fentanyl analogue composition will preferably be a preferred composition as indicated herein. The content of fentanyl or at least one analogue or derivative thereof, such as alfentanil, sulfentanil and remifentanil, will typically be around 10 to 200 µg per hour of depot duration, preferably 25 to 100 µg per hour duration for a duration of 24 to 170 hours, preferably 48 to 120 (e.g. 72) hours. Fentanyl analogue depots may be administered by i.m. or s.c. injection, or preferably by epidural catheter.

The invention further provides a method of treatment comprising administration of a fentanyl analogue composition as described above, especially in a subject in need thereof. The method of treatment is particularly for the treatment of pain, especially chronic pain or postoperative pain, where epidural administration may be preferred. The invention also provides the use of a fentanyl analogue composition as described above in the manufacture of a medicament for the treatment of pain, especially chronic pain or postoperative pain, where epidural administration may be preferred. The invention additionally provides for a pre-filled administration device as indicated herein and a kit as indicated herein comprising the fentanyl analogue composition.

In a still further aspect, the invention also provides a pre-formulation, comprising a low viscosity mixture of:
 a) at least one diacyl glycerol;
 b) at least one phosphatidyl choline;
 c) at least one oxygen containing organic solvent;
 d) finasteride or at least one analogue or derivative thereof;
 wherein the pre-formulation forms, or is capable of forming, at least one liquid crystalline phase structure upon contact with an aqueous fluid. The finasteride analogue composition will preferably be a preferred composition as indicated herein. The content of finasteride will typically be around 10 to 100 mg per week of depot duration, preferably 15 to 60 mg per week duration for a duration of 4 to 24 weeks, preferably 8 to 16 (e.g. 12) weeks.

The invention further provides a method of treatment comprising administration of a finasteride analogue composition as described above, especially in a subject in need thereof. The method of treatment is particularly for the treatment of male pattern baldness and/or enlarged prostate. The invention also provides the use of a finasteride analogue composition as described above in the manufacture of a medicament for the treatment of male pattern baldness and/or enlarged prostate. The invention additionally provides for a pre-filled administration device as indicated herein and a kit as indicated herein comprising the finasteride analogue composition.

In a still further aspect, the invention also provides a pre-formulation, comprising a low viscosity mixture of:

a) at least one diacyl glycerol;
b) at least one phosphatidyl choline;
c) at least one oxygen containing organic solvent;
d) interferon beta, or at least one analogue or derivative thereof;

wherein the pre-formulation forms, or is capable of forming, at least one liquid crystalline phase structure upon contact with an aqueous fluid.

The interferon beta analogue composition will preferably be a preferred composition as indicated herein. The content of interferon beta or analogue will typically be around 0.5 to 10 mg per week of depot duration, preferably 0.7 to 5 mg per week duration for a duration of 4 to 24 weeks, preferably 8 to 16 (e.g. 12) weeks.

The invention further provides a method of treatment comprising administration of a interferon beta analogue composition as described above, especially in a subject in need thereof. The method of treatment is particularly for the treatment of multiple sclerosis. The invention also provides the use of a interferon beta analogue composition as described above in the manufacture of a medicament for the treatment of multiple sclerosis. The invention additionally provides for a pre-filled administration device as indicated herein and a kit as indicated herein comprising the interferon beta analogue composition.

In a still further aspect, the invention also provides a pre-formulation, comprising a low viscosity mixture of:
a) at least one diacyl glycerol;
b) at least one phosphatidyl choline;
c) at least one oxygen containing organic solvent;
d) at least one dopamine agonist;

wherein the pre-formulation forms, or is capable of forming, at least one liquid crystalline phase structure upon contact with an aqueous fluid.

The dopamine agonist composition will preferably be a preferred composition as indicated herein. The content of dopamine agonist, such as pramipexole will typically be around 1 to 100 mg per week of depot duration, preferably 2 to 50 mg per week duration for a duration of 4 to 24 weeks, preferably 8 to 16 (e.g. 12) weeks.

The invention further provides a method of treatment comprising administration of a dopamine agonist composition as described above, especially in a subject in need thereof. The method of treatment is particularly for the treatment of parkinson's disease. The invention also provides the use of a interferon beta analogue composition as described above in the manufacture of a medicament for the treatment of parkinson's disease. The invention additionally provides for a pre-filled administration device as indicated herein and a kit as indicated herein comprising the dopamine agonist composition.

In a still further aspect, the invention also provides a pre-formulation, comprising a low viscosity mixture of:
a) at least one diacyl glycerol;
b) at least one phosphatidyl choline;
c) at least one oxygen containing organic solvent;
d) somatotropin, or at least one analogue or derivative thereof;

wherein the pre-formulation forms, or is capable of forming, at least one liquid crystalline phase structure upon contact with an aqueous fluid.

The somatotropin analogue composition will preferably be a preferred composition as indicated herein. The content of somatotropin or analogue will typically be around 0.1 to 10 mg per week of depot duration, preferably 0.2 to 8 mg per week duration for a duration of 4 to 24 weeks, preferably 8 to 16 (e.g. 12) weeks.

The invention further provides a method of treatment comprising administration of a somatotropin analogue composition as described above, especially in a subject in need thereof. The method of treatment is particularly for the treatment of human growth hormone deficiency and short stature in children and adults. The invention also provides the use of a somatotropin analogue composition as described above in the manufacture of a medicament for the treatment of human growth hormone deficiency and short stature in children and adults. The invention additionally provides for a pre-filled administration device as indicated herein and a kit as indicated herein comprising the somatotropin analogue composition.

In a still further aspect, the invention also provides a pre-formulation, comprising a low viscosity mixture of:
a) at least one diacyl glycerol;
b) at least one phosphatidyl choline;
c) at least one oxygen containing organic solvent;
d) an alpha-agonist such as clonidine, or at least one analogue or derivative thereof;

wherein the pre-formulation forms, or is capable of forming, at least one liquid crystalline phase structure upon contact with an aqueous fluid.

The clonidine analogue composition will preferably be a preferred composition as indicated herein. The content of clonidine or analogue will typically around 0.2 to 50 mg per week of depot duration, preferably 0.7 to 25 mg per week duration for a duration of 4 to 24 weeks, preferably 8 to 16 (e.g. 12) weeks.

The invention further provides a method of treatment comprising administration of a clonidine analogue composition as described above, especially in a subject in need thereof. The method of treatment is particularly for the treatment of hypertension. The invention also provides the use of a clonidine analogue composition as described above in the manufacture of a medicament for the treatment of hypertension. The invention additionally provides for a pre-filled administration device as indicated herein and a kit as indicated herein comprising the clonidine analogue composition. The ability to tailor the dose of the depot to individual patients is particularly important with alpha-agonist compositions.

In a still further aspect, the invention also provides a pre-formulation, comprising a low viscosity mixture of:
a) at least one diacyl glycerol;
b) at least one phosphatidyl choline;
c) at least one oxygen containing organic solvent;
d) naltrexone, or at least one analogue or derivative thereof;

wherein the pre-formulation forms, or is capable of forming, at least one liquid crystalline phase structure upon contact with an aqueous fluid.

The naltrexone analogue composition will preferably be a preferred composition as indicated herein. The content of naltrexone or analogue will typically around 70 to 1000 mg per week of depot duration, preferably 350 to 750 mg per week duration for a duration of 1 to 6 weeks, preferably 1 to 4 (e.g. 2) weeks.

The invention further provides a method of treatment comprising administration of a naltrexone analogue composition as described above, especially in a subject in need thereof. The method of treatment is particularly for the treatment of opoid addiction and/or dependence. The invention also provides the use of a naltrexone analogue composition as described above in the manufacture of a medicament for the treatment of opoid addiction and/or dependence. The invention additionally provides for a pre-filled administration device as indicated herein and a kit as indicated herein comprising the naltrexone analogue composition.

In a still further aspect, the invention also provides a pre-formulation, comprising a low viscosity mixture of:
  a) at least one diacyl glycerol;
  b) at least one phosphatidyl choline;
  c) at least one oxygen containing organic solvent;
  d) a taxol, or at least one analogue or derivative thereof;
wherein the pre-formulation forms, or is capable of forming, at least one liquid crystalline phase structure upon contact with an aqueous fluid.

The taxol analogue composition will preferably be a preferred composition as indicated herein. The content of taxol or analogue will typically be paclitaxel or a structurally related derivative and be present at around 20 to 120 mg per week of depot duration, preferably 35 to 80 mg per week duration for a duration of 1 to 12 weeks, preferably 1 to 8 (e.g. 3 or 6) weeks.

The invention further provides a method of treatment comprising administration of a taxol analogue composition as described above, especially in a subject in need thereof. The method of treatment is particularly for the treatment of cancers, such as node-positive breast cancer, ovarian cancer, non-small-cell lung cancer and/or Kaposi's sarcoma. The invention also provides the use of a naltrexone analogue composition as described above in the manufacture of a medicament for the treatment of cancers, such as node-positive breast cancer, ovarian cancer, non-small-cell lung cancer and/or Kaposi's sarcoma. The invention additionally provides for a pre-filled administration device as indicated herein and a kit as indicated herein comprising the taxol analogue composition. The ability to tailor the administered dose to the patient at the point of delivery is very important in this aspect of the invention, since dosages are typically by body surface area.

In a still further aspect, the invention also provides a pre-formulation, comprising a low viscosity mixture of:
  a) at least one diacyl glycerol;
  b) at least one phosphatidyl choline;
  c) at least one oxygen containing organic solvent;
  d) bupivacaine or at least one analogue or derivative thereof, such as levobupivacaine;
wherein the pre-formulation forms, or is capable of forming, at least one liquid crystalline phase structure upon contact with an aqueous fluid.

The bupivacaine analogue composition will preferably be a preferred composition as indicated herein. The content of bupivacaine or at least one analogue or derivative thereof, will typically be around 5 to 200 mg per hour of depot duration, preferably 10 to 100 mg per hour duration for a duration of 16 to 170 hours, preferably 48 to 120 (e.g. 72) hours. bupivacaine analogue depots may be administered by i.m. or s.c. injection, or by epidural catheter or other appropriate route.

The invention further provides a method of treatment comprising administration of a bupivacaine analogue composition as described above, especially in a subject in need thereof. The method of treatment is particularly for the treatment of pain, especially chronic pain or postoperative pain, where epidural administration may be appropriate. The invention also provides the use of a bupivacaine analogue composition as described above in the manufacture of a medicament for the treatment of pain, especially chronic pain or postoperative pain, where epidural administration may be appropriate. The invention additionally provides for a pre-filled administration device as indicated herein and a kit as indicated herein comprising the bupivacaine analogue composition.

In a still further aspect, the invention also provides a pre-formulation, comprising a low viscosity mixture of:
  a) at least one diacyl glycerol;
  b) at least one phosphatidyl choline;
  c) at least one oxygen containing organic solvent;
  d) GLP-1, or at least one analogue, receptor agonist or derivative thereof;
wherein the pre-formulation forms, or is capable of forming, at least one liquid crystalline phase structure upon contact with an aqueous fluid.

The GLP-1 analogue composition will preferably be a preferred composition as indicated herein. The content of GLP-1 or analogue will typically be around 0.05 to 10 mg per week of depot duration, preferably 0.1 to 8 mg per week duration for a duration of 1 to 24 weeks, preferably 2 to 16 (e.g. 12) weeks.

Glucagon-like peptide (GLP)-1 is a potent glucoregulatory hormone that is released from intestinal L cells into the circulation in response to nutrient ingestion and neural and endocrine stimuli. Structurally, GLP-1 is a 37-amino acid peptide with a MW of 4.2 KDa, having a sequence highly conserved between different species. GLP-1 is involved in modification of glucose homeostasis through actions that include potentiation of glucose-stimulated insulin secretion and biosynthesis and suppression of glucagon secretion, gastric emptying, and food intake. The abilities of GLP-1 to stimulate insulin secretion and inhibit glucagon release are glucose-dependent; thus, the risk of hypoglycemia with GLP-1 administration is low. GLP-1 also increases beta-cell mass in preclinical models of diabetes through mechanisms that include stimulation of beta-cell proliferation and neogenesis and inhibition of beta-cell apoptosis. Studies in both animals and humans indicate that GLP-1 may also play a protective role in the cardiovascular system.

The combined actions of GLP-1 have generated substantial interest in using this peptide as a therapeutic agent for the treatment of type 2 diabetes. However, the therapeutic potential of native GLP-1 is limited by its very short plasma half-life (below 2 minutes). This is due to both rapid inactivation by the proteolytic enzyme dipeptidyl peptidase (DPP)-IV and renal clearance. Consequently, long-acting, DPP-IV-resistant GLP-1 analogs have been developed for clinical use, including exenatide (Byetta, Amylin-Lilly), liraglutide (Novo Nordisk), CJC-1131 (ConjuChem), AVE010 (Zealand Pharma—Sanofi-Aventis), LY548806 (Lilly), and TH-0318 (TheraTechnologies). All these are once- or twice-daily administration products; a controlled-release (one week) exentide product (Alkermes-Amylin-Lilly) is currently under clinical investigation. These GLP-1 mimetics bind to GLP-1 receptors with similar affinity and produce biological actions identical to those of native GLP-1 but are resistant to DPP-IV-mediated inactivation and renal clearance.

These compounds are able to exert more sustained GLP-1-like activity for longer periods of time in vivo. An alternative therapeutic approach for prolonging the action of native GLP-1 is to inhibit DPP-IV activity, thereby preventing GLP-1 degradation. Several orally active agents that inhibit DPP-IV activity are being evaluated for the treatment of type 2 diabetes.

The invention further provides a method of treatment comprising administration of a GLP-1 analogue, composition as described above, especially in a subject in need thereof. The method of treatment is particularly for the treatment of diabetes, especially type II diabetes. The invention also provides the use of a GLP-1 analogue composition as described above in the manufacture of a medicament for the treatment of diabetes, especially type II diabetes. The invention additionally provides for a pre-filled administration device as indicated herein and a kit as indicated herein comprising the GLP-1 analogue composition.

The Invention will now be further illustrated by reference to the following non-limiting Examples and the attached Figures, in which.

EXAMPLES

Figure 1:
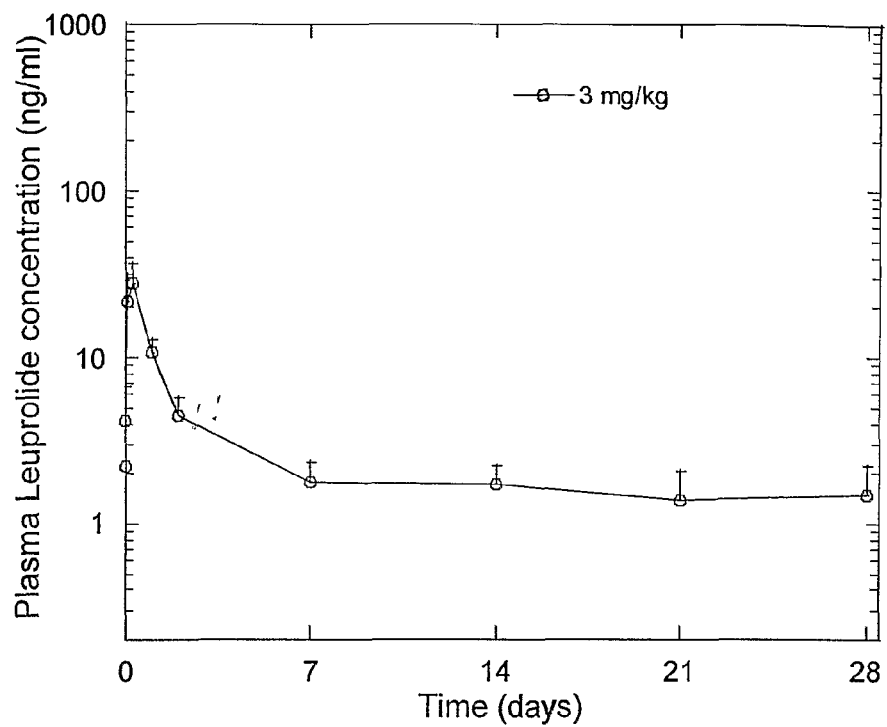
FIG. 1 shows leuprolide plasma levels in the rat model following administration of leuprolide formulation precursor (0.3 wt % in leuprolide).

Example 1: Availability of Various Liquid Crystalline Phases in the Depot by Choice of Composition Injectable formulations containing different proportions of phosphatidyl choline ("PC"—Lipoid S100) and glycerol dioleate (GDO) and with EtOH as solvent were prepared to illustrate that various liquid crystalline phases can be accessed after equilibrating the depot precursor formulation with excess water.

Appropriate amounts of PC, GDO and EtOH were weighed in glass vials and the mixture was placed on a shaker until the PC completely dissolved to form a clear liquid solution. GDO was then added to form an injectable homogenous solution.

Each formulation was injected in a vial and equilibrated with excess water. The phase behaviour was evaluated visually and between crossed polarizes at 25° C. Results are presented in Table 1.

TABLE 1

| Formulation | PC (wt %) | GDO (wt %) | EtOH (wt %) | Phase in H$_2$O |
|---|---|---|---|---|
| A | 22.5 | 67.5 | 10.0 | L$_2$ |
| B | 28.8 | 61.2 | 10.0 | I$_2$ |
| C | 45.0 | 45.0 | 10.0 | I$_2$/H$_{II}$ |
| D | 63.0 | 27.0 | 10.0 | H$_{II}$/L$_\alpha$ |

L$_2$ = reversed micellar phase
I$_2$ = reversed cubic liquid crystalline phase
H$_{II}$ = reversed hexagonal liquid crystalline phase
L$_\alpha$ = lamellar phase Example 2: Viscosity in PC/GDO Mixtures on Addition of Co-Solvent Mixtures of PC/GDO and co-solvent were prepared according to the methods of Example 1. The EtOH content was adjusted by first evaporating the EtOH from the PC/GDO-mixture on a rotary evaporator leaving a viscous liquid mixture of essentially only PC and GDO. Co-solvents were then added in the proportions indicated in Table 2 below.

The samples were allowed to equilibrate for several days before viscosity measurements were performed using a Physica UDS 200 rheometer at 25° C.

TABLE 2

| Sample | PC/GDO (wt/wt) | EtOH/ wt % | Glycerol/ wt % | H$_2$O/ wt % | Viscosity/ mPas |
|---|---|---|---|---|---|
| 1 | 50/50 | 3 | — | — | 1900 |
| 2 | 50/50 | 5 | — | — | 780 |
| 3 | 50/50 | 7 | — | — | 430 |
| 4 | 50/50 | 8 | — | — | 300 |
| 5 | 50/50 | 10 | — | — | 210 |
| 6 | 50/50 | 15 | — | — | 100 |
| 7 | 45/55 | 3 | — | — | 1350 |
| 8 | 45/55 | 5 | — | — | 540 |
| 9 | 45/55 | 7 | — | — | 320 |
| 10 | 45/55 | 8 | — | — | 250 |
| 11 | 45/55 | 10 | — | — | 150 |
| 12 | 45/55 | 15 | — | — | 85 |
| 13 | 40/60 | 3 | — | — | 740 |
| 14 | 40/60 | 5 | — | — | 400 |
| 15 | 40/60 | 7 | — | — | 240 |
| 16 | 40/60 | 8 | — | — | 200 |
| 17 | 40/60 | 10 | — | — | 130 |
| 18 | 40/60 | 15 | — | — | 57 |
| 19 | 40/60 | — | 10 | — | $8 * 10^6$ |
| 20 | 40/60 | — | — | 3 | $2.5 * 10^8$ |
| 21 | 40/60 | — | — | 5 | $4 * 10^7$ |

This example illustrates the need for a solvent with viscosity lowering properties in order to obtain injectable formulations. The mixtures containing glycerol (sample 19) or water (samples 20 and 21) are too viscous to be injectable at solvent concentrations equivalent to the samples containing EtOH (compare with samples 13, 14 and 17).

Example 3: Preparation of Depot Compositions Containing the Peptide Leuprolide

Leuprolide acetate is an acetate salt of a synthetic nonapeptide and an analogue of gonadotropin-releasing hormone (GnRH) (also known as luteinizing hormone-releasing hormone (LHRH)). As a result of leuprolide administration to a subject, there is an initial increase in follicle stimulating hormone (FSH) and luteinizing hormone (LH) secretion (so-called flare effect) which in turn stimulates the production of testosterone by the testes in men and estrogens by ovaries in women. After about 10 days, a profound hypogonadal effect, equivalent to surgical castration, is achieved through down-regulation. Generally this induced and reversible hypogonadism is the therapeutic goal.

Leuprolide was first mixed with PC, GDO and EtOH where EtOH was added in excess to dissolve the peptide and the lipids to give a homogenous and clear solution. Typically, the EtOH content at this stage was about 50-80 wt %. The excess EtOH was then removed by rotary evaporation or freeze-drying and the final EtOH content was thereafter adjusted as required. The final compositions of the samples are given in Table 3 below.

TABLE 3

| Formulation | Leuprolide/wt % | PC/wt % | GDO/wt % | EtOH/wt % |
|---|---|---|---|---|
| A | 0.30 | 47.35 | 47.35 | 5.0 |
| B | 0.66 | 47.17 | 47.17 | 5.0 |
| C | 2.0 | 46.5 | 46.5 | 5.0 |
| D | 4.5 | 45.25 | 45.25 | 5.0 |
| E | 6.0 | 44.5 | 44.5 | 5.0 |

Injecting the formulation precursor into excess aqueous phase (syringe 23 G; 0.6 mm×30 mm) resulted in a monolithic liquid crystalline phase i.e. leuprolide did not change monolith formation and phase behaviour after exposure to an aqueous environment.

The leuprolide depot precursor formulations in this Example were tested for stability against crystallization during storage. Each formulation was stable at 4-8° C. for at least two weeks.

Example 4: In Vivo Release Study from Depot Formulation Containing Leuprolide Subcutaneously Administered In an in vivo rat model the drug release of leuprolide was followed during 28 days. The formulation was administered subcutaneously between the scapulae by using a syringe (23 G, 0.6 mm×25 mm). The leuprolide concentration in the rat plasma was followed for a period of 28 days (see FIG. 1). The dose was 3 mg/kg and the dose volume 1 ml/kg corresponding to a drug load of 0.3 wt % leuprolide in the depot formulation precursor (Formulation A in Example 3).

FIG. 1 shows leuprolide plasma levels in the rat model following administration of leuprolide formulation precursor (0.3 wt % in leuprolide). It appears that the investigated formulation gives a release profile with a minimal initial release (low "burst") and a sustained release duration of at least 28 days.

Example 5: Preparation of Depot Compositions Containing the Peptide Goserelin Goserelin is a potent synthetic decapeptide analogue of luteinizing hormone-releasing hormone (LHRH), also known as a GnRH agonist analogue. Goserelin binds to the gonadotropin releasing hormone (GnRH) receptor and, after prolonged administration, inhibits endogenous secretion of gonadotropin, resulting in suppression of sex hormone production in the ovary and testes. This agent reduces testosterone production to castration levels and may inhibit androgen receptor-positive tumor progression.

Goserelin was first mixed with PC, GDO and EtOH where EtOH was added in excess to dissolve the peptide and the lipids to give a homogenous and clear solution. The EtOH content at this stage was about 50-80 wt %. The excess EtOH was then removed by rotary evaporation or freeze-drying and the final EtOH content was thereafter adjusted as required. The final compositions of the samples are given in Table 4 below.

TABLE 4

| Formulation | Goserelin/wt % | PC/wt % | GDO/wt % | EtOH/wt % |
| --- | --- | --- | --- | --- |
| A | 1.08 | 46.96 | 46.96 | 5.00 |
| B | 2.16 | 46.42 | 46.42 | 5.00 |
| C | 4.32 | 45.34 | 45.34 | 5.00 |

Injecting the formulation precursor into excess aqueous phase (syringe 23 G; 0.6 mm×30 mm) resulted in a monolithic liquid crystalline phase i.e. goserelin did not change monolith formation and phase behaviour after exposure to an aqueous environment.

The goserelin depot precursor formulations in this Example were tested for stability against crystallization during storage. Each formulation was stable at 4-8° C. for at least two weeks.

Example 6: Preparation of Depot Compositions Containing the Peptide Triptorelin Triptorelin is a potent synthetic decapeptide analogue of luteinizing hormone-releasing hormone (LHRH), also known as a GnRH agonist analogue. Triptorelin binds to the gonadotropin releasing hormone (GnRH) receptor and, after prolonged administration, inhibits endogenous secretion of gonadotropin, resulting in suppression of sex hormone production in the ovary and testes. This agent reduces testosterone production to castration levels and may inhibit androgen receptor-positive tumor progression.

Triptorelin was first mixed with PC, GDO and EtOH where EtOH was added in excess to dissolve the peptide and the lipids to give a homogenous and clear solution. The EtOH content at this stage was about 50-80 wt %. The excess EtOH was then removed by rotary evaporation or freeze-drying and the final EtOH content was thereafter adjusted as required. The final compositions of the samples are given in Table 5 below.

TABLE 5

| Formulation | Triptorelin/wt % | PC/wt % | GDO/wt % | EtOH/wt % |
| --- | --- | --- | --- | --- |
| A | 0.75 | 47.125 | 47.125 | 5.00 |
| B | 1.5 | 46.75 | 46.75 | 5.00 |

Injecting the formulation precursor into excess aqueous phase (syringe 23 G; 0.6 mm×30 mm) resulted in a monolithic liquid crystalline phase i.e. triptorelin did not change monolith formation and phase behaviour after exposure to an aqueous environment.

The triptorelin depot precursor formulations in this Example were tested for stability against crystallization during storage. Each formulation was stable at 4-8° C. for at least two weeks.

Example 7: Preparation of Depot Compositions Containing the Peptide Buserelin Buserelin is a highly potent synthetic nonapeptide analogue of luteinizing hormone-releasing hormone (LHRH), also known as a GNRH agonist analogue. Buserelin binds to the gonadotropin releasing hormone (GnRH) receptor and, after prolonged administration, inhibits endogenous secretion of gonadotropin, resulting in suppression of sex hormone production in the ovary and testes. This agent reduces testosterone production to castration levels and may inhibit androgen receptor-positive tumor progression.

Buserelin was first mixed with PC, GDO and EtOH where EtOH was added in excess to dissolve the peptide and the lipids to give a homogenous and clear solution. The EtOH content at this stage was about 50-80 wt %. The excess EtOH was then removed by rotary evaporation or freeze-drying and the final EtOH content was thereafter adjusted as required. The final compositions of the samples are given in Table 6 below.

TABLE 6

| Formulation | Buserelin/wt % | PC/wt % | GDO/wt % | EtOH/wt % |
| --- | --- | --- | --- | --- |
| A | 0.66 | 47.17 | 47.17 | 5.00 |
| B | 1.32 | 46.84 | 46.84 | 5.00 |
| C | 1.98 | 46.51 | 46.51 | 5.00 |

Injecting the formulation precursor into excess aqueous phase (syringe 23 G; 0.6 mm×30 mm) resulted in a monolithic liquid crystalline phase i.e. buserelin did not change monolith formation and phase behaviour after exposure to an aqueous environment.

The buserelin depot precursor formulations in this Example were tested for stability against crystallization during storage. Each formulation was stable at 4-8° C. for at least two weeks.

Example 8: Degradation of Depot Formulation in the Rat

Various volumes (1, 2, 6 ml/kg) of the depot precursor (36% wt PC, 54% wt GDO, and 10% wt EtOH) were injected in the rat and were removed again after a period of 14 days. It was found that substantial amounts of the formulations were still present subcutaneously in the rat after this time, see Table 7.

TABLE 7

| Dose (ml/kg) | Mean diameter day 3 (mm) | Mean diameter day 14 (mm) |
|---|---|---|
| 1 (n = 3) | 15.8 | 12.5 |
| 2 (n = 3) | 18.5 | 15.3 |
| 6 (n = 3) | 23.3 | 19.3 |

Example 8B: Further Compositions Containing GnRH Agonist Analogues

Formulations were prepared as described in Examples 3, 5, 6 and 7 by mixing the peptide active with a mixture of GDO (at one of several purity levels), PC, ethanol and optionally dioleoyl PG in the proportions (by weight) indicated in Table 8.

TABLE 8

| Formulation | Peptide | EtOH | PC | GDO1 | GDO2 | GDO3 | DOPG |
|---|---|---|---|---|---|---|---|
| 1 | 2.25 (LEU) | 10 | 35.1 | — | — | 52.65 | — |
| 2 | 2.25 (LEU) | 10 | 35.1 | 52.65 | — | — | — |
| 3 | 2.25 (LEU) | 10 | 35.1 | — | 52.65 | — | — |
| 4 | 2.25 (LEU) | 7 | 36.3 | — | — | 54.45 | — |
| 5 | 2.16 (GOS) | 10 | 35.14 | — | — | 52.70 | — |
| 6 | 2.16 (GOS) | 7 | 36.34 | — | — | 54.50 | — |
| 7 | 2.16 (GOS) | 5 | 37.14 | — | — | 55.70 | — |
| 8 | 1.50 (TRI) | 10 | 35.4 | — | — | 53.1 | — |
| 9 | 1.50 (TRI) | 7 | 36.6 | — | — | 54.9 | — |
| 10 | 1.50 (TRI) | 5 | 37.4 | — | — | 56.1 | — |
| 11 | 1.32 (BUS) | 10 | 35.47 | — | — | 53.21 | — |
| 12 | 1.32 (BUS) | 7 | 36.67 | — | — | 55.01 | — |
| 13 | 1.32 (BUS) | 5 | 37.47 | — | — | 56.21 | — |
| 14 | 2.25 (LEU) | 10 | 39.49 | — | — | 48.26 | — |
| 15 | 2.25 (LEU) | 5 | 45.375 | — | — | 45.375 | 2 |
| 16 | 2.25 (LEU) | 5 | 44.375 | — | — | 44.375 | 4 |

Abbreviations:
LEU = Leuprolide;
GOS = Goserelin;
TRI = Triptorelin;
BUS = Buserelin
where EtOH is ethanol, PC is LIPOID S100 soybean phosphatidylcholine, GDO is glycerol dioleate and DOPG is dioleoyl phosphatidylglycerol

| GDO quality (according to AC) | Monoglycerides | Diglycerides | Triglycerides |
|---|---|---|---|
| GDO1 | 10.9% | 87.5% | 1.4% |
| GDO2 | 4.2% | 92.1% | 3.5% |
| GDO3 | 0.5% | 95.3% | 4.0% |

Example 8C: Preparation of Depot Compositions of Glucagon-Like Peptide 1 (GLP-1)

Depot precursors of GLP-1 were prepared in two different ways:

1) GLP-1 was first mixed with PC, GDO and EtOH where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.

2) GLP-1 was first dissolved in a small amount of sterile water. A pre-made liquid mixture of PC, GDO and EtOH, where the EtOH content was about 5-10% by weight, was then added to the GLP-1/water solution. The resulting mixture was mixed by vortex mixing for 1 min.

The final compositions of the samples are given in Table 9 below. Several purity levels of GDO and both soy and egg phosphatidylcholine (PC) were used.

TABLE 9

Compositions containing GLP-1

| Formulation | GLP-1/ wt % | PC/ wt % | GDO1/ wt % | GDO2/ wt % | GDO3/ wt % | EtOH/ wt % | $H_2O$/ wt % |
|---|---|---|---|---|---|---|---|
| A | 0.5 | 44.75 | 44.75 | — | — | 10 | — |
| B | 0.5 | 44.75 | — | 44.75 | — | 10 | — |
| C | 0.5 | 44.75 | — | — | 44.75 | 10 | — |
| D | 1.0 | 44.5 | — | — | 44.5 | 10 | — |
| E | 1.0 | 46 | — | — | 46 | 7 | — |
| F | 1.0 | 47 | — | — | 47 | 5 | — |
| G | 2.0 | 44 | — | — | 44 | 10 | — |
| H | 2.0 | 45.5 | — | — | 45.5 | 7 | — |
| I | 2.0 | 46.5 | — | — | 46.5 | 5 | — |
| J | 3.0 | 46 | — | — | 46 | 5 | — |
| K | 0.5 | 35.775 | — | — | 43.725 | 10 | 10 |
| L | 1.0 | 35.55 | — | — | 43.45 | 10 | 10 |
| M | 2.0 | 37.35 | — | — | 45.65 | 5 | 10 |
| N | 2.0 | 32.85 | — | — | 40.15 | 10 | 15 |
| O | 2.0 | 30.4 | — | — | 45.6 | 10 | 12 |
| P | 3.0 | 30 | — | — | 45 | 10 | 12 |
| Q | 3.0 | 31.875 | — | — | 43.125 | 10 | 12 |

TABLE 9-continued

Compositions containing GLP-1

| Formulation | GLP-1/wt % | PC/wt % | GDO1/wt % | GDO2/wt % | GDO3/wt % | EtOH/wt % | H$_2$O/wt % |
|---|---|---|---|---|---|---|---|
| R | 3.0 | 32.4 | — | — | 39.6 | 10 | 15 |
| S | 2.0* | 46.5 | — | — | 46.5 | 5 | — |
| T | 2.0* | 32.85 | — | — | 40.15 | 10 | 15 |
| U | 2.0* | 30.4 | — | — | 45.6 | 10 | 12 | where EtOH is ethanol, PC is LIPOID S100 soybean phosphatidylcholine or LIPOID E 80 egg phosphatidylcholine (marked with *) and GDO is glycerol dioleate

TABLE 10

GDO qualities used

| GDO quality (according to AC) | Monoglycerides | Diglycerides | Triglycerides |
|---|---|---|---|
| GDO1 | 10.9% | 87.5% | 1.4% |
| GDO2 | 4.2% | 92.1% | 3.5% |
| GDO3 | 0.5% | 95.3% | 4.0% |

Example 9: Preparation of Depot Compositions of Paclitaxel

Depot precursors of paclitaxel were prepared by mixing paclitaxel, PC, GDO and EtOH where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.

The final compositions of the samples are given in Table 11 below. Both soy and egg phosphatidylcholine (PC) were used in the compositions.

TABLE 11

Compositions containing paclitaxel

| Formulation | Paclitaxel/wt % | PC/wt % | GDO3/wt % | EtOH/wt % |
|---|---|---|---|---|
| A | 0.5 | 44.75 | 44.75 | 10 |
| B | 0.5 | 46.25 | 46.25 | 7 |
| C | 0.5 | 47.25 | 47.25 | 5 |
| D | 0.5 | 37.8 | 56.7 | 5 |
| E | 0.5* | 47.25 | 47.25 | 5 |
| F | 1.0 | 44.5 | 44.5 | 10 |
| G | 1.0 | 46 | 46 | 7 |
| H | 1.0 | 47 | 47 | 5 |
| I | 1.0 | 37.6 | 56.4 | 5 |
| J | 1.0* | 47 | 47 | 5 |
| K | 2.0 | 44 | 44 | 10 |
| L | 2.0 | 45.5 | 45.5 | 7 |
| M | 2.0 | 46.5 | 46.5 | 5 |
| N | 2.0 | 37.2 | 55.8 | 5 |
| O | 2.0* | 46.5 | 46.5 | 5 |
| P | 5 | 42.5 | 42.5 | 10 |
| Q | 5 | 44 | 44 | 7 |
| R | 5 | 45 | 45 | 5 |
| S | 5 | 36 | 54 | 5 |
| T | 5* | 45 | 45 | 5 |
| U | 10 | 40 | 40 | 10 |

TABLE 11-continued

Compositions containing paclitaxel

| Formulation | Paclitaxel/wt % | PC/wt % | GDO3/wt % | EtOH/wt % |
|---|---|---|---|---|
| V | 10 | 41.5 | 41.5 | 7 |
| W | 10 | 42.5 | 42.5 | 5 |
| X | 10 | 34 | 51 | 5 |
| Y | 10* | 42.5 | 42.5 | 5 | where EtOH is ethanol, PC is LIPOID S100 soybean phosphatidylcholine or LIPOID E 80 egg phosphatidylcholine (marked with *) and GDO is glycerol dioleate (see below)

| GDO quality (according to AC) | Monoglycerides | Diglycerides | Triglycerides |
|---|---|---|---|
| GDO3 | 0.5% | 95.3% | 4.0% |

Example 10: Preparation of Depot Compositions of Interferon Beta 1A

Depot precursors of interferon beta 1A were prepared in two different ways:

1) Interferon beta 1A was first mixed with PC, GDO and EtOH where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.

2) Interferon beta 1A was first dissolved in a small amount of sterile water. A pre-made liquid mixture of PC, GDO and EtOH, where the EtOH content was about 5-10% by weight, was then added to the Interferon beta 1A/water solution. The resulting mixture was mixed by vortex mixing for 1 min.

The final compositions of the samples are given in Table 12 below. Both soy and egg phosphatidylcholine (PC) were used.

TABLE 12

Compositions containing interferon beta 1A

| Formulation | Interferon beta 1A/wt % | PC/wt % | GDO3/wt % | EtOH/wt % | H$_2$O/wt % |
|---|---|---|---|---|---|
| A | 0.03 | 44.985 | 44.985 | 10 | — |
| B | 0.03 | 46.485 | 46.485 | 7 | — |
| C | 0.03 | 47.485 | 47.485 | 5 | — |
| D | 0.05 | 44.975 | 44.975 | 10 | — |
| E | 0.05 | 46.475 | 46.475 | 7 | — |
| F | 0.05 | 47.475 | 47.475 | 5 | — |
| G | 0.1 | 37.96 | 56.94 | 5 | — |
| H | 0.1 | 47.45 | 47.45 | 5 | — |
| I | 0.1* | 37.96 | 56.94 | 5 | — |
| J | 0.1* | 47.45 | 47.45 | 5 | — |
| K | 0.05 | 35.98 | 43.97 | 10 | 10 |
| L | 0.05 | 37.98 | 45.97 | 10 | 10 |
| M | 0.05 | 31.98 | 47.97 | 10 | 10 |
| N | 0.1 | 35.96 | 43.94 | 10 | 10 |
| O | 0.1 | 31.96 | 47.94 | 10 | 10 |
| P | 0.1* | 35.96 | 43.94 | 10 | 10 |
| Q | 0.1* | 31.96 | 47.94 | 10 | 10 |
| R | 0.2 | 33.9 | 45.9 | 10 | 10 |
| S | 0.2 | 35.9 | 43.9 | 10 | 10 | where EtOH is ethanol, PC is LIPOID S100 soybean phosphatidylcholine or LIPOID E 80 egg phosphatidylcholine (marked with *) and GDO is glycerol dioleate (see below)

| GDO quality (according to AC) | Monoglycerides | Diglycerides | Triglycerides |
|---|---|---|---|
| GDO3 | 0.5% | 95.3% | 4.0% |

Example 11: Preparation of Depot Compositions of Human Growth Hormone (hGH)

Depot precursors of hGH were prepared in two different ways:
1) hGH was first mixed with PC, GDO and EtOH where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.
2) hGH was first mixed in a small amount of sterile water. A pre-made liquid mixture of PC, GDO and EtOH, where the EtOH content was about 5-10% by weight, was then added to the hGH/water mixture. The resulting mixture was mixed by vortex mixing for 1 min.

The final compositions of the samples are given in Table 13 below. Both soy and egg phosphatidylcholine (PC) were used.

TABLE 13

Compositions containing hGH

| Formulation | hGH/wt % | PC/wt % | GDO3/wt % | EtOH/wt % | H$_2$O/wt % |
|---|---|---|---|---|---|
| A | 0.5 | 44.75 | 44.75 | 10 | — |
| B | 0.5 | 46.25 | 46.25 | 7 | — |
| C | 0.5 | 47.25 | 47.25 | 5 | — |
| D | 0.5 | 33.53 | 40.97 | 10 | 15 |
| E | 0.5 | 35.78 | 43.72 | 10 | 10 |
| F | 0.5 | 37.13 | 45.37 | 7 | 10 |
| G | 1 | 47 | 47 | 5 | — |
| H | 1 | 31.6 | 47.4 | 10 | 10 |
| I | 1 | 34.65 | 42.35 | 10 | 12 |
| J | 1 | 33.75 | 41.25 | 10 | 14 |
| K | 1 | 33.3 | 40.7 | 10 | 15 |
| L | 1* | 34.65 | 42.35 | 10 | 12 |
| M | 1.2 | 34.68 | 39.12 | 10 | 15 |
| N | 1.2 | 33.21 | 40.59 | 10 | 15 |
| O | 1.2* | 34.68 | 39.12 | 10 | 15 |
| P | 1.2* | 33.21 | 40.59 | 10 | 15 | where EtOH is ethanol, PC is LIPOID S100 soybean phosphatidylcholine or LIPOID E 80 egg phosphatidylcholine (marked with *) and GDO is glycerol dioleate (see below)

| GDO quality (according to AC) | Monoglycerides | Diglycerides | Triglycerides |
|---|---|---|---|
| GDO3 | 0.5% | 95.3% | 4.0% |

Example 12: Preparation of Depot Compositions of Naltrexone

Depot precursors of naltrexone were prepared by mixing naltrexone, PC, GDO and EtOH where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.

The final compositions of the samples are given in Table 14 below.

TABLE 14

Compositions containing naltrexone

| Formulation | Naltrexone/wt % | PC/wt % | GDO3/wt % | EtOH/wt % |
|---|---|---|---|---|
| A | 5 | 42.5 | 42.5 | 10 |
| B | 5 | 44 | 44 | 7 |
| C | 5 | 45 | 45 | 5 |
| D | 5 | 36 | 54 | 5 |
| E | 5* | 45 | 45 | 5 |
| F | 10 | 40 | 40 | 10 |
| G | 10 | 41.5 | 41.5 | 7 |
| H | 10 | 42.5 | 42.5 | 5 |
| I | 10 | 34 | 51 | 5 |
| J | 10* | 42.5 | 42.5 | 5 |
| K | 15 | 37.5 | 37.5 | 10 |
| L | 15 | 39 | 39 | 7 |
| M | 15 | 40 | 40 | 5 |
| N | 15 | 32 | 48 | 5 |
| O | 15* | 40 | 40 | 5 |
| P | 20 | 35 | 35 | 10 |
| Q | 20 | 36.5 | 36.5 | 7 |
| R | 20 | 37.5 | 37.5 | 5 |
| S | 20 | 30 | 45 | 5 |
| T | 20* | 37.5 | 37.5 | 5 | where EtOH is ethanol, PC is LIPOID S100 soybean phosphatidylcholine or LIPOID E 80 egg phosphatidylcholine (marked with *) and GDO is glycerol dioleate (see below)

| GDO quality (according to AC) | Monoglycerides | Diglycerides | Triglycerides |
|---|---|---|---|
| GDO3 | 0.5% | 95.3% | 4.0% |

Example 13: Preparation of Depot Compositions of Bupivacaine and Levobupivacaine Depot precursors of bupivacaine (or levobupivacaine) were prepared by mixing bupivacaine or levobupivacaine, PC, GDO and EtOH where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.

The final compositions of the samples are given in Table 15 below. Both soy and egg phosphatidylcholine (PC) were used in the compositions.

TABLE 15

Compositions containing bupivacaine or levobupivacaine

| Formulation | Bupivacaine or levobupivacaine/wt % | PC/wt % | GDO3/wt % | EtOH/wt % |
|---|---|---|---|---|
| A | 5 | 42.5 | 42.5 | 10 |
| B | 5 | 44 | 44 | 7 |
| C | 5 | 45 | 45 | 5 |
| D | 5 | 36 | 54 | 5 |
| E | 5* | 45 | 45 | 5 |
| F | 10 | 40 | 40 | 10 |
| G | 10 | 41.5 | 41.5 | 7 |
| H | 10 | 42.5 | 42.5 | 5 |
| I | 10 | 34 | 51 | 5 |
| J | 10* | 42.5 | 42.5 | 5 |
| K | 15 | 37.5 | 37.5 | 10 |
| L | 15 | 39 | 39 | 7 |

TABLE 15-continued

Compositions containing bupivacaine or levobupivacaine

| Formulation | Bupivacaine or levobupivacaine/ wt % | PC/ wt % | GDO3/ wt % | EtOH/ wt % |
|---|---|---|---|---|
| M | 15 | 40 | 40 | 5 |
| N | 15 | 32 | 48 | 5 |
| O | 15* | 40 | 40 | 5 | where EtOH is ethanol, PC is LIPOID S100 soybean phosphatidylcholine or LIPOID E 80 egg phosphatidylcholine (marked with *) and GDO is glycerol dioleate (see below)

| GDO quality (according to AC) | Monoglycerides | Diglycerides | Triglycerides |
|---|---|---|---|
| GDO3 | 0.5% | 95.3% | 4.0% |

Example 14: Preparation of Depot Compositions of Pramipexole

Depot precursors of pramipexole were prepared by mixing pramipexole, PC, GDO and EtOH where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.

The final compositions of the samples are given in Table 16 below. Both soy and egg phosphatidylcholine (PC) were used in the compositions.

TABLE 16

Compositions containing pramipexole

| Formulation | Pramipexole/ wt % | PC/wt % | GDO3/wt % | EtOH/wt % |
|---|---|---|---|---|
| A | 1.0 | 44.5 | 44.5 | 10 |
| B | 1.0 | 46 | 46 | 7 |
| C | 1.0 | 47 | 47 | 5 |
| D | 1.0 | 37.6 | 56.4 | 5 |
| E | 1.0* | 47 | 47 | 5 |
| F | 3 | 43.5 | 43.5 | 10 |
| G | 3 | 45 | 45 | 7 |
| H | 3 | 46 | 46 | 5 |
| I | 3 | 36.8 | 55.2 | 5 |
| J | 3* | 46 | 46 | 5 |
| K | 5 | 42.5 | 42.5 | 10 |
| L | 5 | 44 | 44 | 7 |
| M | 5 | 45 | 45 | 5 |
| N | 5 | 36 | 54 | 5 |
| O | 5* | 45 | 45 | 5 | where EtOH is ethanol, PC is LIPOID S100 soybean phosphatidylcholine or LIPOID E 80 egg phosphatidylcholine (marked with *) and GDO is glycerol dioleate (see below)

| GDO quality (according to AC) | Monoglycerides | Diglycerides | Triglycerides |
|---|---|---|---|
| GDO3 | 0.5% | 95.3% | 4.0% |

Example 15: Preparation of Depot Compositions of Clonidine

Depot precursors of clonidine were prepared by mixing clonidine, PC, GDO and EtOH where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.

The final compositions of the samples are given in Table 17 below. Both soy and egg phosphatidylcholine (PC) were used in the compositions.

TABLE 17

Compositions containing clonidine

| Formulation | Clonidine/ wt % | PC/wt % | GDO3/wt % | EtOH/wt % |
|---|---|---|---|---|
| A | 1.0 | 44.5 | 44.5 | 10 |
| B | 1.0 | 46 | 46 | 7 |
| C | 1.0 | 47 | 47 | 5 |
| D | 1.0 | 37.6 | 56.4 | 5 |
| E | 1.0* | 47 | 47 | 5 |
| F | 3 | 43.5 | 43.5 | 10 |
| G | 3 | 45 | 45 | 7 |
| H | 3 | 46 | 46 | 5 |
| I | 3 | 36.8 | 55.2 | 5 |
| J | 3* | 46 | 46 | 5 |
| K | 5 | 42.5 | 42.5 | 10 |
| L | 5 | 44 | 44 | 7 |
| M | 5 | 45 | 45 | 5 |
| N | 5 | 36 | 54 | 5 |
| O | 5* | 45 | 45 | 5 | where EtOH is ethanol, PC is LIPOID S100 soybean phosphatidylcholine or LIPOID E 80 egg phosphatidylcholine (marked with *) and GDO is glycerol dioleate (see below)

| GDO quality (according to AC) | Monoglycerides | Diglycerides | Triglycerides |
|---|---|---|---|
| GDO3 | 0.5% | 95.3% | 4.0% |

Example 16: Preparation of Depot Compositions of Levothyroxine

Depot precursors of levothyroxine were prepared by mixing levothyroxine, PC, GDO and EtOH where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.

The final compositions of the samples are given in Table 18 below. Both soy and egg phosphatidylcholine (PC) were used in the compositions.

TABLE 18

Compositions containing levothyroxine

| Formulation | Levothyroxine/ wt % | PC/wt % | GDO3/wt % | EtOH/wt % |
|---|---|---|---|---|
| A | 0.5 | 44.75 | 44.75 | 10 |
| B | 0.5 | 46.25 | 46.25 | 7 |
| C | 0.5 | 47.25 | 47.25 | 5 |
| D | 0.5 | 37.8 | 56.7 | 5 |
| E | 0.5* | 47.25 | 47.25 | 5 |
| F | 1.5 | 44.25 | 44.25 | 10 |
| G | 1.5 | 45.75 | 45.75 | 7 |
| H | 1.5 | 46.75 | 46.75 | 5 |
| I | 1.5 | 37.4 | 56.1 | 5 |
| J | 1.5* | 46.75 | 46.75 | 5 |
| K | 3 | 43.5 | 43.5 | 10 |
| L | 3 | 45 | 45 | 7 |

TABLE 18-continued

Compositions containing levothyroxine

| Formulation | Levothyroxine/wt % | PC/wt % | GDO3/wt % | EtOH/wt % |
|---|---|---|---|---|
| M | 3 | 46 | 46 | 5 |
| N | 3 | 36.8 | 55.2 | 5 |
| O | 3* | 46 | 46 | 5 | where EtOH is ethanol, PC is LIPOID S100 soybean phosphatidylcholine or LIPOID E 80 egg phosphatidylcholine (marked with *) and GDO is glycerol dioleate (see below)

| GDO quality (according to AC) | Monoglycerides | Diglycerides | Triglycerides |
|---|---|---|---|
| GDO3 | 0.5% | 95.3% | 4.0% |

Example 17: Preparation of Depot Compositions of Buprenorphine

Depot precursors of buprenorphine were prepared by mixing buprenorphine, PC, GDO and EtOH where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.

The final compositions of the samples are given in Table 19 below. Both soy and egg phosphatidylcholine (PC) were used in the compositions.

TABLE 19

Compositions containing buprenorphine

| Formulation | Buprenorphine/wt % | PC/wt % | GDO3/wt % | EtOH/wt % |
|---|---|---|---|---|
| A | 1.0 | 44.5 | 44.5 | 10 |
| B | 1.0 | 46 | 46 | 7 |
| C | 1.0 | 47 | 47 | 5 |
| D | 1.0 | 37.6 | 56.4 | 5 |
| E | 1.0* | 47 | 47 | 5 |
| F | 3 | 43.5 | 43.5 | 10 |
| G | 3 | 45 | 45 | 7 |
| H | 3 | 46 | 46 | 5 |
| I | 3 | 36.8 | 55.2 | 5 |
| J | 3* | 46 | 46 | 5 |
| K | 5 | 42.5 | 42.5 | 10 |
| L | 5 | 44 | 44 | 7 |
| M | 5 | 45 | 45 | 5 |
| N | 5 | 36 | 54 | 5 |
| O | 5* | 45 | 45 | 5 | where EtOH is ethanol, PC is LIPOID S100 soybean phosphatidylcholine or LIPOID E 80 egg phosphatidylcholine (marked with *) and GDO is glycerol dioleate (see below)

| GDO quality (according to AC) | Monoglycerides | Diglycerides | Triglycerides |
|---|---|---|---|
| GDO3 | 0.5% | 95.3% | 4.0% |

Example 18: Preparation of Depot Compositions of Testosterone Esters

Depot precursors of the undecanoate and enanthate esters of testosterone were prepared by mixing the testosterone esters, PC, GDO and EtOH, where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.

The final compositions of the samples are given in Table 20 below. Both soy and egg phosphatidylcholine (PC) were used in the compositions.

TABLE 20

Compositions containing testosterone undecanoate or testosterone enanthate

| Formulation | Testosterone undecanoate or testosterone enanthate/wt % | PC/wt % | GDO3/wt % | EtOH/wt % |
|---|---|---|---|---|
| A | 10 | 40 | 40 | 10 |
| B | 10 | 41.5 | 41.5 | 7 |
| C | 10 | 42.5 | 42.5 | 5 |
| D | 10 | 34 | 51 | 5 |
| E | 10* | 42.5 | 42.5 | 5 |
| F | 15 | 37.5 | 37.5 | 10 |
| G | 15 | 39 | 39 | 7 |
| H | 15 | 40 | 40 | 5 |
| I | 15 | 32 | 48 | 5 |
| J | 15* | 40 | 40 | 5 |
| K | 20 | 35 | 35 | 10 |
| L | 20 | 36.5 | 36.5 | 7 |
| M | 20 | 37.5 | 37.5 | 5 |
| N | 20 | 30 | 45 | 5 |
| O | 20* | 37.5 | 37.5 | 5 |
| P | 25 | 32.5 | 32.5 | 10 |
| Q | 25 | 34 | 34 | 7 |
| R | 25 | 35 | 35 | 5 |
| S | 25 | 28 | 42 | 5 |
| T | 25* | 35 | 35 | 5 | where EtOH is ethanol, PC is LIPOID S100 soybean phosphatidylcholine or LIPOID E 80 egg phosphatidylcholine (marked with *) and GDO is glycerol dioleate (see below)

| GDO quality (according to AC) | Monoglycerides | Diglycerides | Triglycerides |
|---|---|---|---|
| GDO3 | 0.5% | 95.3% | 4.0% |

Example 19: In Vivo Release Study from Depot Formulations Containing Testosterone Esters Subcutaneously Administered In an in vivo rat model the drug release of testosterone undecanoate and testosterone enanthate was followed during 28 days. The formulations were administered subcutaneously between the scapulae by using a syringe (23 G, 0.6 mm×25 mm). The testosterone concentration in the rat plasma was followed for a period of 28 days (see FIG. 2). The dose was 125 mg/kg and the dose volume 0.5 ml/kg corresponding to a drug load of 25 wt % testosterone ester in the depot formulation precursor (Formulation R in Example 18).

Figure 2:
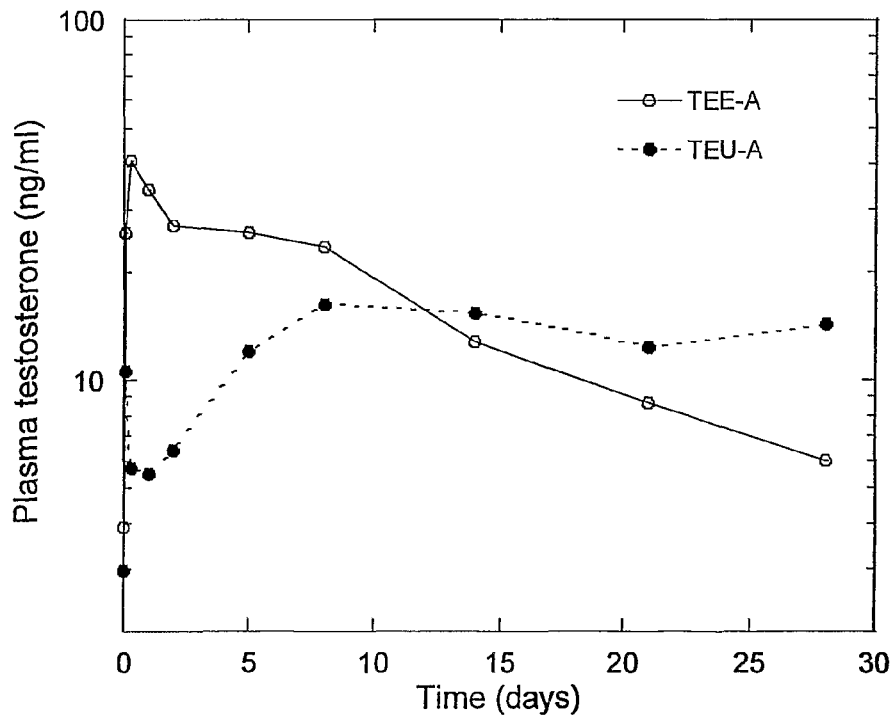
FIG. 2 shows testosterone plasma levels in the rat model following administration of testosterone undecanoate (TEU) and testosterone enanthate (TEE) formulation precursors (25 wt % in testosterone ester).

FIG. 2 shows testosterone plasma levels in the rat model following administration of testosterone undecanoate (TEU) and testosterone enanthate (TEE) formulation precursors (25 wt % in testosterone ester). It appears that the investigated formulations give release profiles with a sustained release duration of at least 28 days.

Example 20: Preparation of a Depot Precursor of hGH Using a 2-Part Mixing Device A depot precursor of hGH was prepared by first dissolving 7.5 mg of hGH in 0.15 g of sterile water. This solution was withdrawn into a 1 mL glass syringe. A liquid solution containing PC, GDO and EtOH (PC/GDO/EtOH=40.5/49.5/10 wt %) (0.84 g) was withdrawn into a second glass syringe.

The two syringes containing hGH/water and the lipid mixture, respectively, were connected using a female to female Luer adapter and the two solutions were mixed by repeatedly pushing the content back and forth. After about 15 cycles of pushing back and forth, the depot precursor was collected in one of the syringes and injected into saline using a 23 gauge needle.

Example 21: Preparation of a Depot Precursor of Interferon Beta 1A Using a 2-Part Mixing Device A depot precursor of interferon beta 1A was prepared by first dissolving 1.0 mg of interferon beta 1A in 0.1 g of sterile water. This solution was withdrawn into a 1 mL glass syringe. A liquid solution containing PC, GDO and EtOH (PC/GDO/EtOH=40.5/49.5/10 wt %) (0.9 g) was withdrawn into a second glass syringe.

The two syringes containing interferon beta 1A/water and the lipid mixture, respectively, were connected using a female to female Luer adapter and the two solutions were mixed by repeatedly pushing the content back and forth. After about 15 cycles of pushing back and forth, the depot precursor was collected in one of the syringes and injected into saline using a 23 gauge needle.

LEGEND TO FIGURES

FIG. 1: Leuprolide plasma levels in the rat model following administration of leuprolide (3 mg/kg) formulation precursor (0.3% by weight leuprolide) according to Example 4.

FIG. 2: Testosterone plasma levels in the rat model following administration of different testosterone derivatives according to Example 19 (TEU=testosterone undecanoate and TEE=testosterone enanthate).

The invention claimed is:

1. A pre-formulation consisting essentially of a low viscosity mixture of:
   a) at least one diacyl glycerol comprising at least 50% glycerol dioleate (GDO);
   b) at least one phosphatidyl choline (PC);
   c) at least one oxygen containing organic solvent comprising ethanol; and
   d) at least one peptide GnRH analogue comprising 12 or fewer amino acids;
wherein the ratio of a:b (w/w) is in the range of 40:60 to 70:30;
wherein the pre-formulation forms at least one liquid crystalline phase structure upon contact with an aqueous fluid.

2. A pre-formulation as claimed in claim 1 wherein component a) comprises at least 80% glycerol dioleate (GDO).

3. A pre-formulation as claimed in claim 1 wherein component b) comprises soy PC.

4. A pre-formulation as claimed in any of claims 1 to 3 wherein said pre-formulation comprises at least one GnRH analogue selected from leuprolide and goserelin.

5. A pre-formulation comprising a low viscosity mixture of:
   a) 40-70 wt. % of at least one diacyl glycerol comprising at least 50% GDO;
   b) 30-60 wt. % of at least one phosphatidyl choline;
   c) at least one oxygen containing organic solvent comprising ethanol;
   d) 0.1-10 wt. % of at least one peptide GnRH analogue comprising 12 or fewer amino acids;
wherein the ratio of a:b (w/w) is in the range of 40:60 to 70:30;
wherein the pre-formulation forms at least one liquid crystalline phase structure upon contact with an aqueous fluid at physiological temperature.

6. A pre-formulation as claimed in claim 5 comprising:
   a) 43-60 wt. % of at least one diacyl glycerol comprising at least 50% GDO;
   b) 35-55 wt. % of at least one phosphatidyl choline;
   c) 0.1-10 wt. % of at least one oxygen containing organic solvent comprising ethanol;
   d) 0.1-10 wt. % of at least one peptide GnRH analogue comprising 12 or fewer amino acids;
wherein the ratio of a:b (w/w) is in the range of 40:60 to 70:30;
wherein the pre-formulation forms, or is capable of forming, at least one liquid crystalline phase structure upon contact with an aqueous fluid.

7. A pre-formulation as claimed in claim 5, wherein the ratio of a:b (w/w) is 45:55 to 60:40.

8. A pre-formulation as claimed in claim 5, wherein the ratio of a:b (w/w) is 48:52 to 55:45.

9. A pre-formulation as claimed in claim 5 wherein component b) comprises soy PC.

10. A pre-formulation as claimed in claim 5 wherein said pre-formulation comprises at least one GnRH analogue selected from leuprolide and goserelin.

11. A pre-formulation comprising a low viscosity mixture of:
   a) 32.5-70 wt. % of at least one diacyl glycerol comprising at least 50% GDO;
   b) 30-60 wt. % of at least one phosphatidyl choline;
   c) at least one oxygen containing organic solvent comprising ethanol;
   d) 0.1-10 wt. % of at least one peptide GnRH analogue comprising 12 or fewer amino acids;
wherein the ratio of a:b (w/w) is in the range of 40:60 to 70:30;
wherein the pre-formulation forms at least one liquid crystalline phase structure upon contact with an aqueous fluid at physiological temperature.

12. A pre-formulation as claimed in claim 11 comprising:
   a) 32.5-60 wt. % of at least one diacyl glycerol comprising at least 50% GDO;
   b) 35-55 wt. % of at least one phosphatidyl choline;
   c) 0.1-10 wt. % of at least one oxygen containing organic solvent comprising ethanol;
   d) 0.1-10 wt. % of at least one peptide GnRH analogue comprising 12 or fewer amino acids;
wherein the ratio of a:b (w/w) is in the range of 40:60 to 70:30;
wherein the pre-formulation forms, or is capable of forming, at least one liquid crystalline phase structure upon contact with an aqueous fluid.

13. A pre-formulation as claimed in claim 11, wherein the ratio of a:b (w/w) is in the range of 45:55 to 60:40.

14. A pre-formulation as claimed in claim 11, wherein the ratio of a:b (w/w) is in the range of 48:52 to 55:45.

15. A pre-formulation as claimed in claim 11 wherein component b) comprises soy PC.

16. A pre-formulation as claimed in claim 11 wherein said pre-formulation comprises at least one peptide GnRH analogue selected from leuprolide and goserelin.

17. A pre-formulation comprising a low viscosity mixture of:

a) 32.5-70 wt. % of at least one diacyl glycerol comprising at least 50% GDO;
b) 30-60 wt. % of at least one phosphatidyl choline;
c) at least one oxygen containing organic solvent comprising ethanol;
d) 0.1-10 wt. % of leuprolide;
wherein the ratio of a:b (w/w) is in the range of 40:60 to 70:30;
wherein the pre-formulation forms at least one liquid crystalline phase structure upon contact with an aqueous fluid at physiological temperature.

18. A pre-formulation as claimed in claim 17 comprising:
a) 32.5-60 wt. % of at least one diacyl glycerol comprising at least 50% GOO;
b) 35-55 wt. % of at least one phosphatidyl choline;
c) 0.1-10 wt. % of at least one oxygen containing organic solvent comprising ethanol;
d) 0.1-10 wt. % of leuprolide;
wherein the ratio of a:b (w/w) is in the range of 40:60 to 70:30;
wherein the pre-formulation forms, or is capable of forming, at least one liquid crystalline phase structure upon contact with an aqueous fluid.

19. A pre-formulation as claimed in claim 17, wherein the ratio of a:b (w/w) is in the range of 45:55 to 60:40.

20. A pre-formulation as claimed in claim 17, wherein the ratio of a:b (w/w) is in the range of 48:52 to 55:45.

21. A pre-formulation as claimed in claim 17 wherein component b) comprises soy PC.

22. A pre-formulation as claimed in claim 14, wherein the at least one peptide GnRH analogue comprising 12 or fewer amino acids is a constrained peptide of 6 to 12 amino acids.

23. A pre-formulation as claimed in claim 22, wherein the at least one peptide GnRH analogue comprises $Gly-NH_2$, $N-Et-NH_2$ or $AzaGly-NH_2$ at the N-terminus.

24. A pre-formulation as claimed in claim 22, wherein the at least one peptide GnRH analogue is selected from GnRH-I, GNRH-II, GnRH III, Fertirelin, Leuprorelin (Leuprolide), Buserelin, Histrelin, Deslorelin, Goserelin, Narafelin and Triptorelin.

* * * * *